United States Patent [19]

Klemarczyk

[11] Patent Number: 4,482,747
[45] Date of Patent: Nov. 13, 1984

[54] SUBSTITUTED METHYL ISOPROPYL OXOCYCLOHEXANE DERIVATIVES, ORGANOLEPTIC USES THEREOF AND PROCESS FOR PREPARING SAME

[75] Inventor: Philip T. Klemarczyk, Old Bridge, N.J.

[73] Assignee: International Flavors & Fragrances Inc., New York, N.Y.

[21] Appl. No.: 551,487

[22] Filed: Nov. 14, 1983

Related U.S. Application Data

[62] Division of Ser. No. 343,571, Apr. 26, 1982, Pat. No. 4,451,403.

[51] Int. Cl.$^3$ ........................................... C07C 49/603
[52] U.S. Cl. ................................................... 568/376
[58] Field of Search ........................................ 568/376

[56] References Cited

U.S. PATENT DOCUMENTS 2,443,015  6/1948  Whitaker et al. .................... 568/376
4,400,545  8/1983  Willis et al. .......................... 568/376

OTHER PUBLICATIONS

Binkley et al., J. Org. Chem., vol. 40(15), pp. 2160–2165, (1975).

Primary Examiner—James H. Reamer
Attorney, Agent, or Firm—Arthur L. Liberman

[57] ABSTRACT

Described is the genus of compounds defined according to the structure:

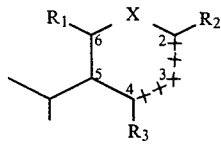

wherein at least one of the lines:

[+ + + +]

represents a carbon-carbon single bond and the other of the lines:

[+ + + +]

represents a carbon-carbon double bond or a carbon-carbon single bond; wherein the moiety X represents one of the moieties:

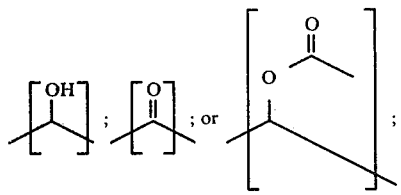

wherein when the moiety X has the structure:

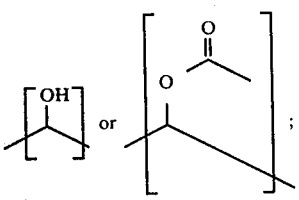

then one of the lines:

[+ + + +]

is a carbon-carbon double bond and the other of the lines:

[+ + + +]

is a carbon-carbon single bond and when the moiety X has the structure:

(Abstract continued on next page)

then both of the lines:

[+ + + +]

represent carbon-carbon single bonds;
wherein, one of $R_1$, $R_2$ and $R_3$ represent 2-methyl-1-propenyl or 2-methyl-1-propylidenyl; and the other of $R_1$, $R_2$ and $R_3$ represent hydrogen; with the provisos that:
(i) when the line:

[+ + + +]

at the 3-4 position is a double bond, then $R_3$ is hydrogen or 2-methyl-1-propenyl; and
(ii) when the line:

[+ + + +]

at the 2-3 position is a double bond, then $R_2$ is hydrogen or 2-methyl-1-propenyl,
with the members of said genus being novel compounds.

1 Claim, 27 Drawing Figures

GLC PROFILE FOR EXAMPLE A.

GLC PROFILE FOR EXAMPLE I.
CRUDE REACTION PRODUCT.

NMR SPECTRUM FOR EXAMPLE A.

IR SPECTRUM FOR EXAMPLE A.

GLC PROFILE FOR EXAMPLE I. (BULKED DISTILLATION FRACTIONS 11-19).

NMR SPECTRUM FOR PEAK 1 OF EXAMPLE I.

IR SPECTRUM FOR PEAK 2 OF EXAMPLE I.

NMR SPECTRUM FOR PEAK 2 OF EXAMPLE I.

IR SPECTRUM FOR EXAMPLE I, PEAK 2.

NMR SPECTRUM FOR PEAK 3 OF EXAMPLE I.

IR SPECTRUM FOR PEAK 3 OF EXAMPLE I.

NMR SPECTRUM FOR PEAK 4A OF EXAMPLE I.

IR SPECTRUM FOR PEAK 4A OF EXAMPLE I.

NMR SPECTRUM FOR PEAK 4B OF EXAMPLE I.

IR SPECTRUM FOR PEAK 4B OF EXAMPLE I.

NMR SPECTRUM FOR PEAK 5 FOR EXAMPLE I.

IR SPECTRUM FOR EXAMPLE I PEAK 5.

GLC PROFILE FOR EXAMPLE II.

GLC PROFILE FOR EXAMPLE I, (BULKED FRACTIONS 11-19).

NMR SPECTRUM FOR MAJOR PEAK OF EXAMPLE II.

IR SPECTRUM FOR MAJOR PEAK FOR EXAMPLE II.

GLC PROFILE FOR EXAMPLE III.

GLC PROFILE FOR EXAMPLE III.

NMR SPECTRUM FOR MAJOR PEAK FOR EXAMPLE IV.

NMR SPECTRUM FOR MAJOR PEAK OF EXAMPLE III.

IR SPECTRUM FOR MAJOR PEAK FOR EXAMPLE III.

IR SPECTRUM FOR MAJOR PEAK FOR EXAMPLE IV.

SUBSTITUTED METHYL ISOPROPYL OXOCYCLOHEXANE DERIVATIVES, ORGANOLEPTIC USES THEREOF AND PROCESS FOR PREPARING SAME

This is a divisional of application Ser. No. 343,571, filed Apr. 26, 1982, now U.S. Pat. No. 4,451,403.

The compounds having the genus defined according to the structure:

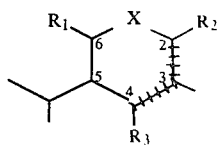

are useful in augmenting or enhancing the aroma or taste of consumable materials including perfume compositions, colognes and perfumed articles (e.g., solid or liquid anionic, cationic, nonionic or zwitterionic detergents, cosmetic powder compositions, fabric softener compositions and fabric softener articles).

Also described is the novel process for preparing compounds defined according to the genus having the structure:

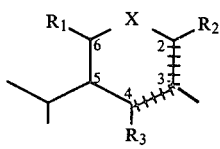

by first dimerizing one or more unsaturated ketones defined according to the structure:

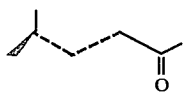

wherein one of the dashed lines is a carbon-carbon double bond and the other of the dashed lines is a carbon-carbon single bond in the presence of an appropriate catalyst such as an alkali metal hydroxide or an alkaline earth metal hydroxide catalyst, aluminum chloride, sulfuric acid or the like to form a mixture of compounds defined according to the structure:

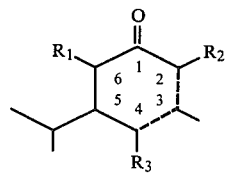

wherein one of the dashed lines represents a carbon-carbon double bond and the other of the dashed lines represents a carbon-carbon single bond; wherein one of $R_1$, $R_2$ and $R_3$ represents 2-methyl-1-propenyl or 2-methyl-1-propylidenyl; and the others of $R_1$, $R_2$ and $R_3$ represent hydrogen with the provisos that:
(i) when the dashed line at the 3-4 position is a double bond, then $R_3$ is hydrogen or 2-methyl-1-propenyl; and
(ii) when the dashed line at the 2-3 position is a double bond, then $R_2$ is hydrogen methyl or 2-methyl-1-propenyl.

and then reducing the compound or mixture of compounds defined according to the structure:

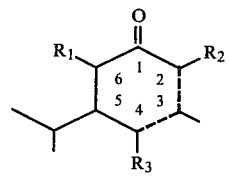

according to the reaction:

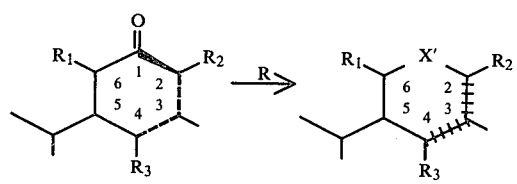

in order to form the compound or mixture of compounds having the structure:

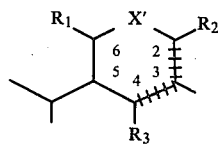

wherein R is either (i) an alkali metal borohydride or (ii) hydrogen in the presence of a palladium catalyst and X' represents one of the moieties:

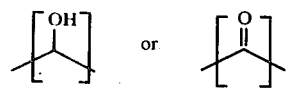 or 

and wherein when X' is the moiety:

R represents an alkali metal borohydride; and when X' is the moiety:

R represents hydrogen in the presence of a palladium catalyst, wherein when both lines [++++] are carbon-carbon single bonds then X' is the moiety:

and when one of the lines [+ + + +] is a carbon-carbon double bond and the other of the lines:

[+ + + +]

is a carbon-carbon single bond then X' has the structure:

BACKGROUND OF THE INVENTION

The instant invention provides substituted methyl isopropyl oxocyclohexane derivatives which are novel, defined according to the structure:

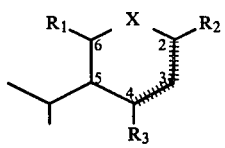

wherein the moiety represents one of the structures:

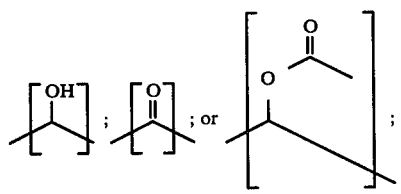

wherein when the moiety X has the structure:

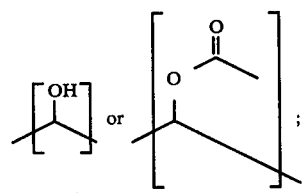

then one of the lines:

[+ + + +]

is a carbon-carbon double bond and the other of the lines:

[+ + + +]

is a carbon-carbon single bond and when the moiety X has the structure:

then both of the lines:

[+ + + +]

represent carbon-carbon single bonds;
wherein, one of $R_1$, $R_2$ and $R_3$ represent 2-methyl-1-propenyl or 2-methyl-1-propylidenyl; and the other of $R_1$, $R_2$ and $R_3$ represent hydrogen; with the provisos that:

(i) when the line:

[+ + + +]

at the 3-4 position is a double bond, then $R_3$ is hydrogen or 2-methyl-1-propenyl; and (ii) when the line:

[+ + + +]

at the 2-3 position is a double bond, then $R_2$ is hydrogen or 2-methyl-1-propenyl, and uses of said substituted methyl isopropyl oxocyclohexane derivatives for their organoleptic properties in augmenting or enhancing the aroma of perfume compositions, perfumed articles or colognes.

Chemical compounds which can provide herbaceous, woody, earthy, camphoraceous, tabac-resin-like, guiacwood-like, cardamom, jute-like, spicy, honey, sweaty, ionone-like, smokey, rosey, vetiver-like, fruity and musky aroma nuances are highly desirable in the art of perfumery. Many of the natural materials which provides such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance, or augment the essential fragrance notes provided by natural essential oils or compositions thereof.

The fundamental problem in creating artificial fragrance agents is that the artificial fragrance to be achieved to be as natural as possible. This generally proves to be a difficult task since the mechanism for a fragrance development in many fragrance materials is not completely known. This is noticeable in products in the fragrance area having herbaceous, woody, earthy, camphoraceous, tobacco resin-like, guiacwood-like, cardamom, jute-like, spicy, honey, sweaty, ionone-like, smokey, rosey, vetiver-like, fruity and musky aroma nuances.

The substituted methyl isopropyl oxocyclohexane derivatives of my invention are not known in the prior art. Although substituted alkyl isopropyl cyclohexanones are known in the prior art, the disclosure of such compounds does not include the utilization thereof in perfumery and, furthermore, does not include processes for producing the substituted alkyl isopropyl cyclohexanones of my invention. Wiemann, et al and Riand and Brun in the references:

(i) Wiemann, et al, Ann. Chim., 1972, Volume 7, pages 399–499, title: "Contributions a L'Etrude des Mechanismes de Condensations Catalytiques de Cetones β-Alkyl α-Ethyleniques en Milieu Heterogene et en Phase Vapeur. Etudes Spectrographiques IR, UV, RMN".

(ii) Riand and Brun, Bulletin de la Societe Chimique de France, 1976, Nos. 3–4 (combined) pages 557–562 inclusive, title: "No. 105—Spectrometrie de Masse. II—Fragmentations Induites par Impact Electronique de Cyclohexenones".

disclose the compounds having the structures:

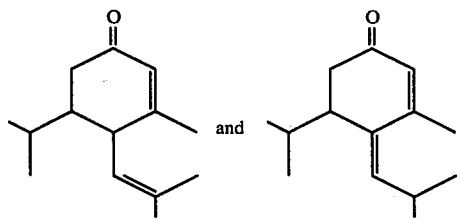

produced by dimerization of the compound having the structure:

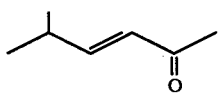

over magnesium oxide dimerization catalyst in the gas phase according to the reaction:

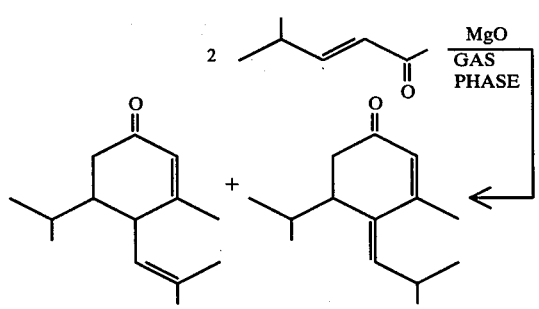

The prior art process of Riand and Brun or Wiemann, et al does not utilize a liquid phase dimerization and does not utilize the catalyst systems of my invention nor does it carry out a reduction of the resultant cyclohexanone. Furthermore, the reaction mixture produced by Riand and Brun or Wiemann does not give rise to the same mixture of compounds which is the starting material for my invention.

Unsaturated cyclic ketones with unsaturated alkylene and alkylidene side chains are known in the field of perfumery; and unsaturated cyclic alkanols and alkanol acetates with unsaturated alkylene and alkylidene side chains are also known in the art of perfumery but these compounds are different in kind in structure from the structures of the compounds of the present invention.

Thus, laevo-carvyl acetate having the structure:

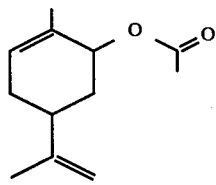

is disclosed by Arctander, "Perfume and Flavor Chemicals (Aroma Chemicals)" at Monograph No. 582 to have a refreshing, green-minty, spearmint-like odor, more "cool" than carvone, not as penetrating but with a peculiar "metallic" undertone . . . sweet, spicy-minty, green and refreshing taste not as powerful as carvone but overall more pleasant, versatile in character". Arctander further states at Monograph No. 578 that laevo-carveol having the structure:

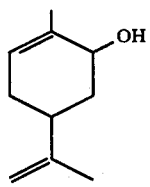

has an odor which is "more caraway-like than spearmint-like (according to the majority of opinions)". Arctander further states that Monograph No. 2770 that iso-pulegone having the structure:

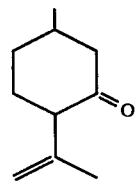

has a "powerful minty, woody, mildly green odor . . . very diffusive and penetrating, not as sweet as pulegone, not as tenacious".

Nothing in the prior art discloses the novel and useful and unexpectedly advantageous organoleptic utilities of the compounds of my invention and nothing in the prior art discloses or renders obvious the novel compounds of my invention or the novel products-by-process of my invention.

is produced wherein in the mixture in each of the molecules one of the dashed lines is a carbon-carbon double bond and the other of the dashed lines is a carbon-carbon single bond and the molecules are different.

Figure 2:
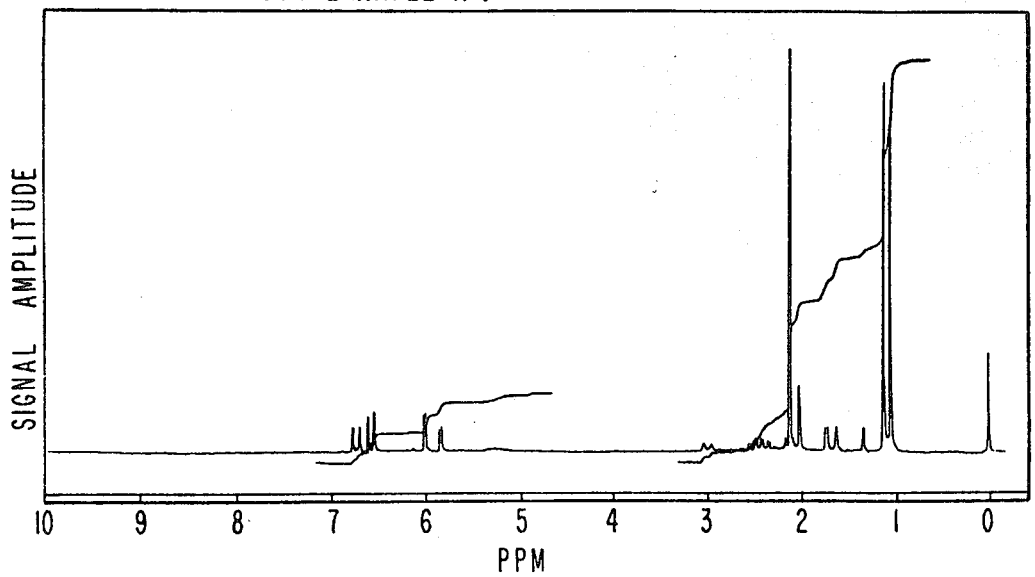

FIG. 2 is the NMR spectrum for the reaction product of Example A containing a mixture of compounds defined according to the structure:

wherein in the mixture in each of the molecules one of the dashed lines is a carbon-carbon double bond and the other of the dashed lines is a carbon-carbon single bond and the components of the mixture are different.

Figure 3:
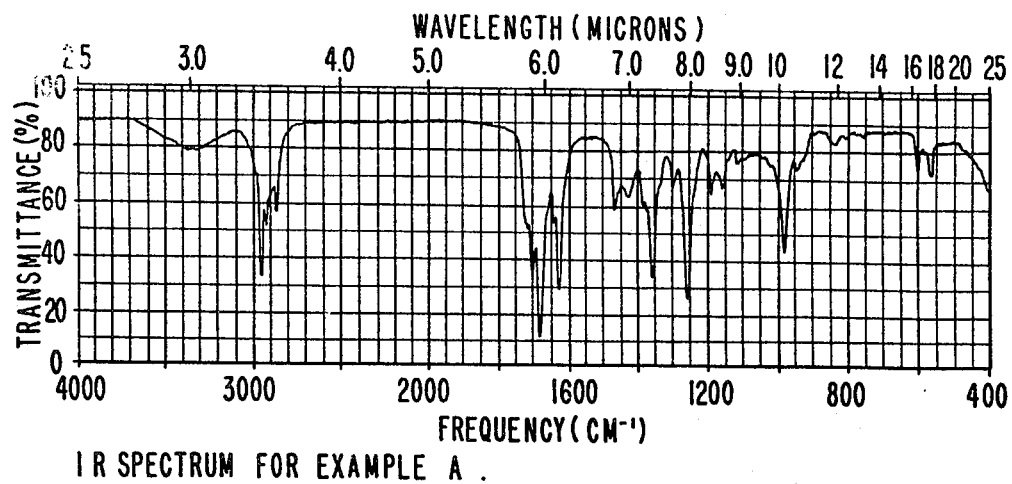

FIG. 3 is the infra-red spectrum for the reaction product of Example A containing the compounds defined according to the structure:

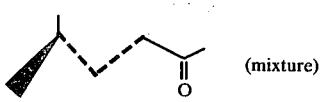 (mixture)

wherein in the mixture in each of molecules, one of the dashed lines is a carbon-carbon double bond and the other of the dashed lines is a carbon-carbon single bond and the compounds are different.

Figure 4:
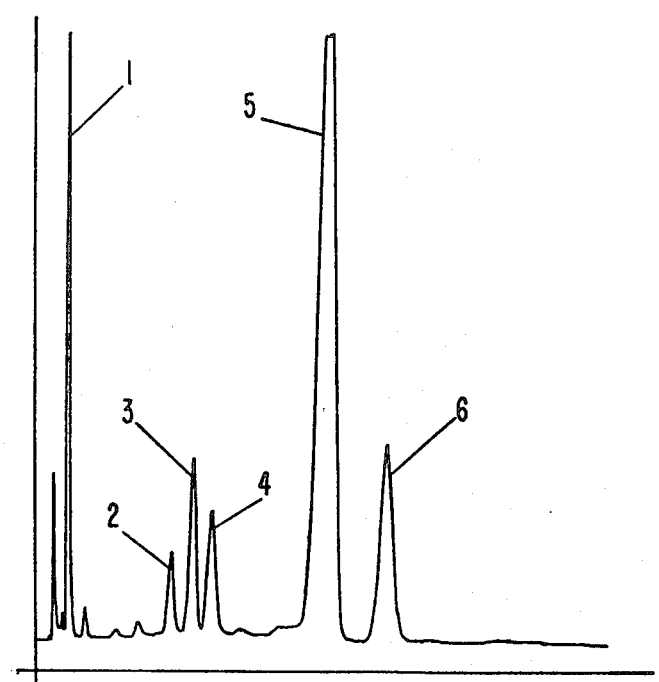

FIG. 4 is the GLC profile for the crude reaction product produced according to Example I containing a mixture of compounds defined according to the structures:

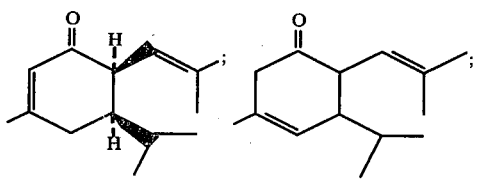

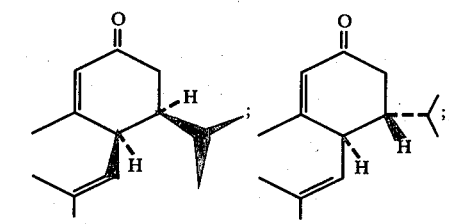

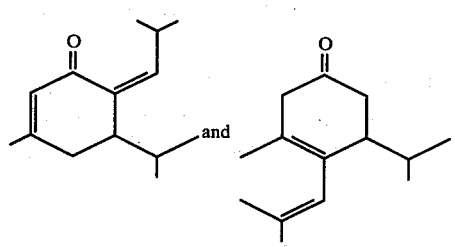 and as well as the mixture of compounds which is the starting material for producing said compounds defined according to the structure:

Figure 5:
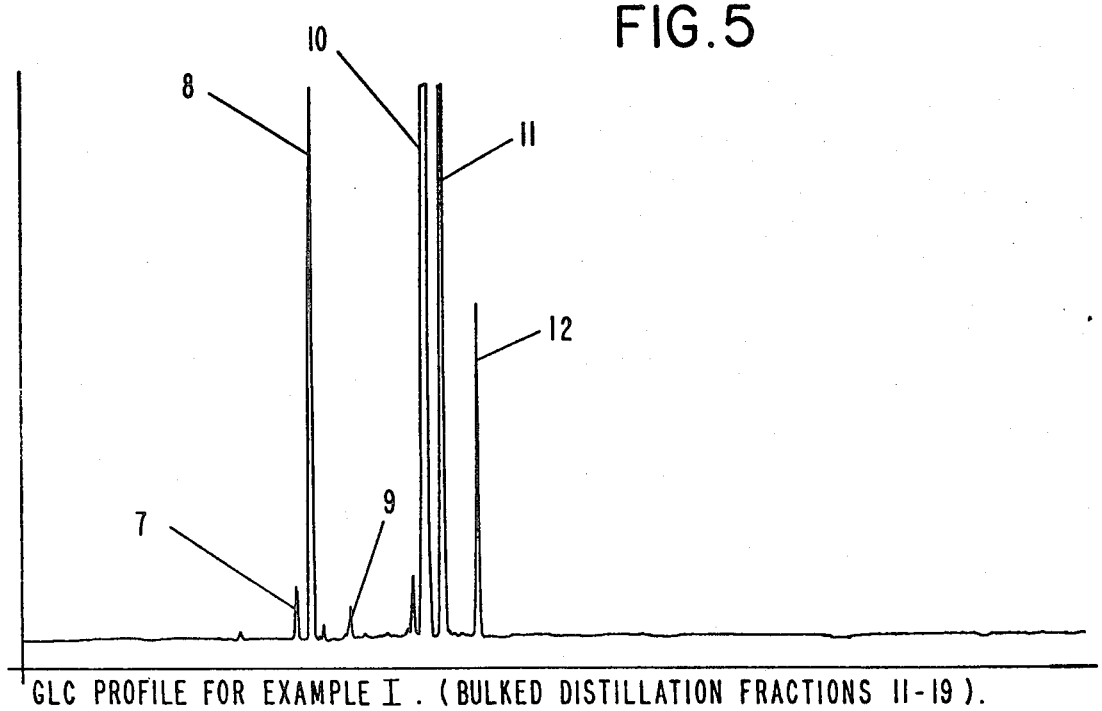

FIG. 5 is the GLC profile for the bulked distillation fractions 11-19 of the distillation product of the reaction product of Example I containing the compounds having the structures:

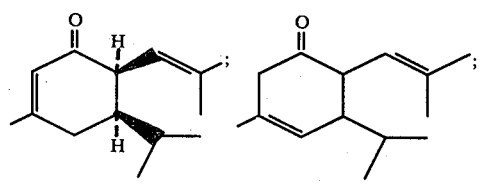

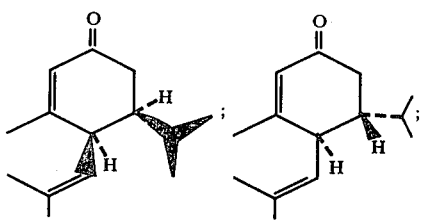

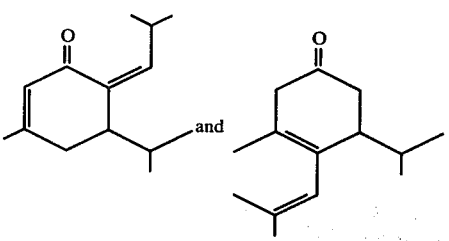 and

Figure 6:
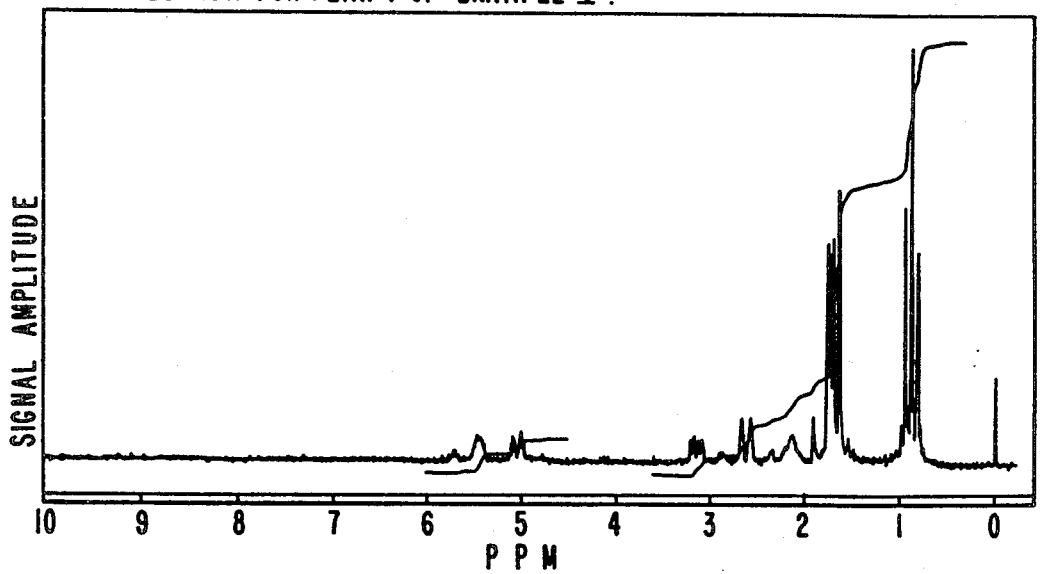

FIG. 6 is the NMR spectrum for Peak 1 (indicated by the reference numeral "2" on the GLC profile of FIG. 4, supra). The compound of Peak 1 has the structure:

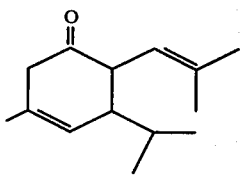

Figure 7:
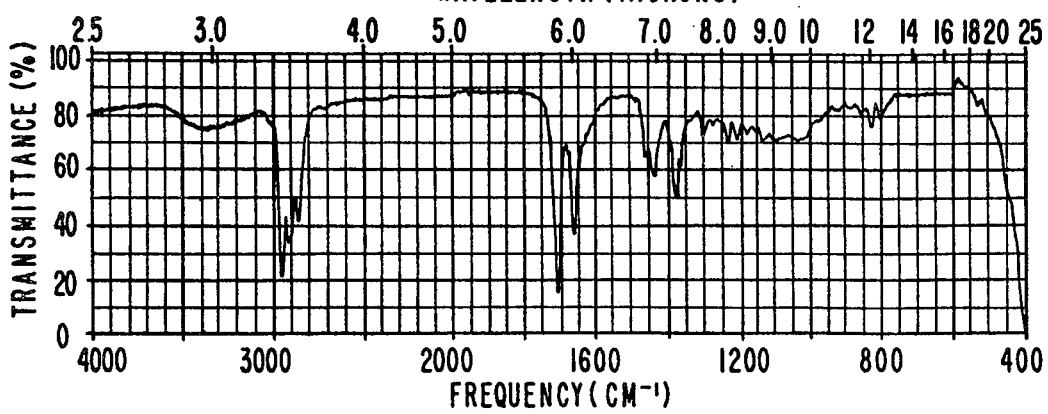

FIG. 7 is the infra-red spectrum for the compound of Peak 1 of the GLC profile of FIG. 4 having the structure:

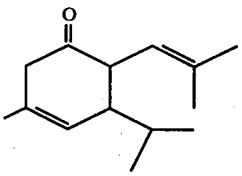

Figure 8:
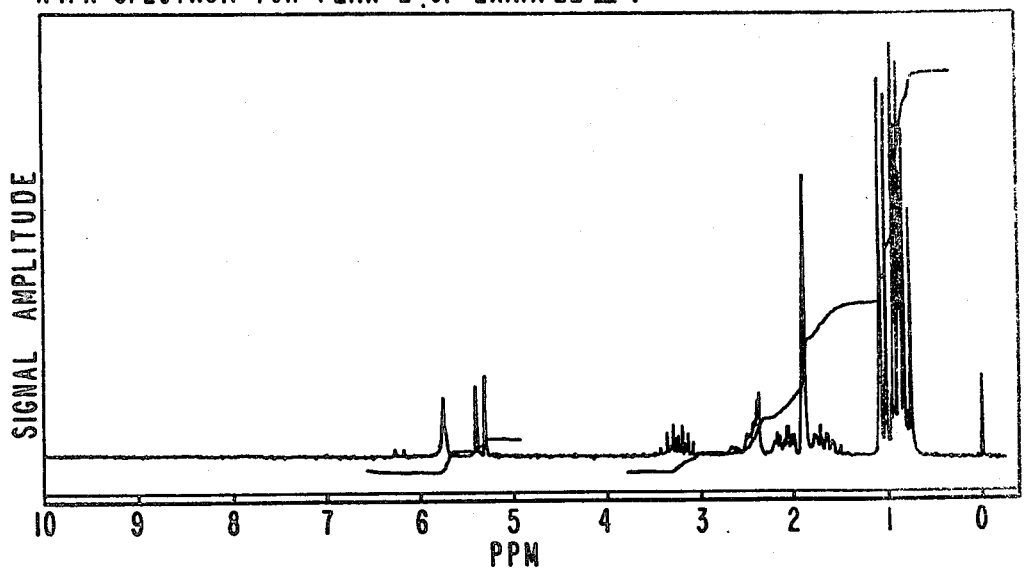

FIG. 8 is the NMR spectrum for Peak 2 of the GLC profile of FIG. 4 which is indicated by reference numeral "3" on said FIG. 4. Peak 2 signifies the compound having the structure:

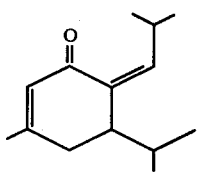

Figure 9:
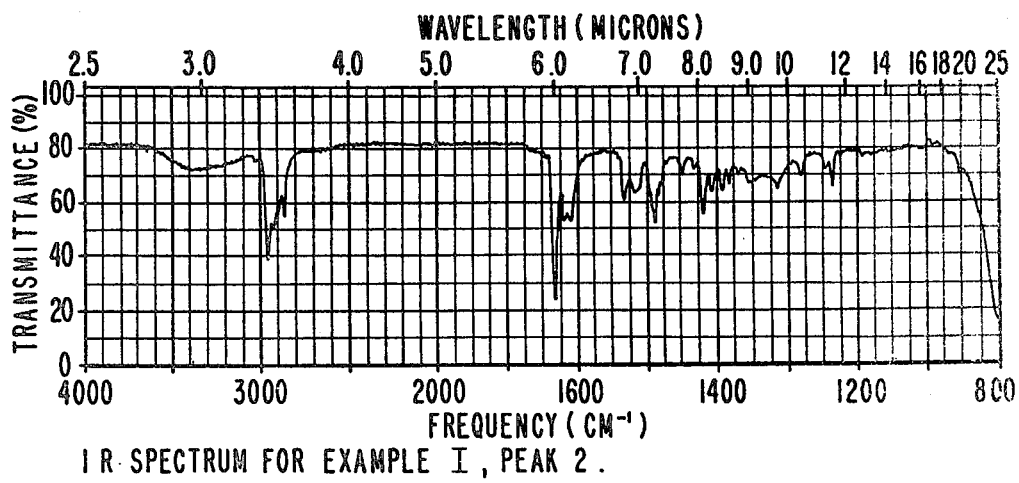

FIG. 9 is the infra-red spectrum for Peak 2 of the GLC profile of FIG. 4, containing the compound having the structure:

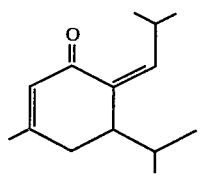

Figure 10:
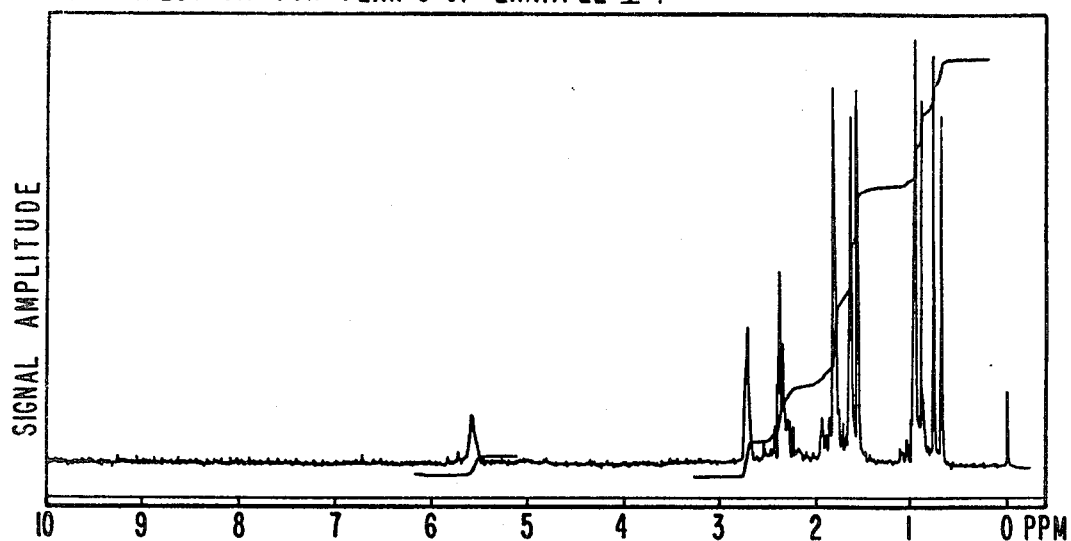

FIG. 10 is the NMR spectrum for Peak 3 of the GLC profile of FIG. 4, with Peak 3 being signified by the reference numeral "4". Peak 3 contains the compound having the structure:

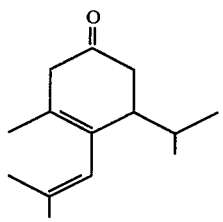

Figure 11:
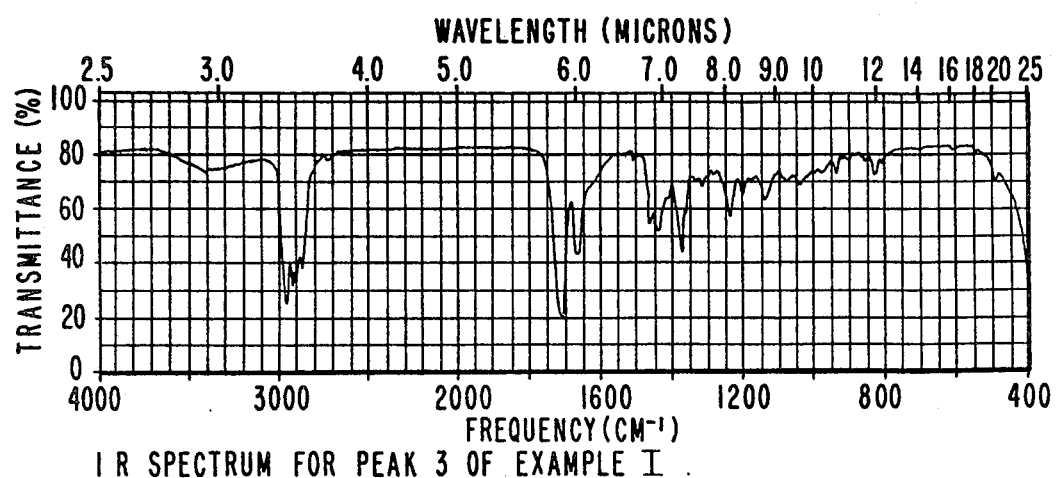

FIG. 11 is the infra-red spectrum for Peak 3 of the GLC profile of FIG. 4 which signifies the compound having the structure:

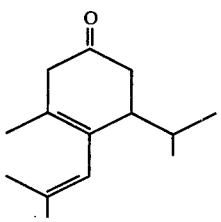

Figure 12:
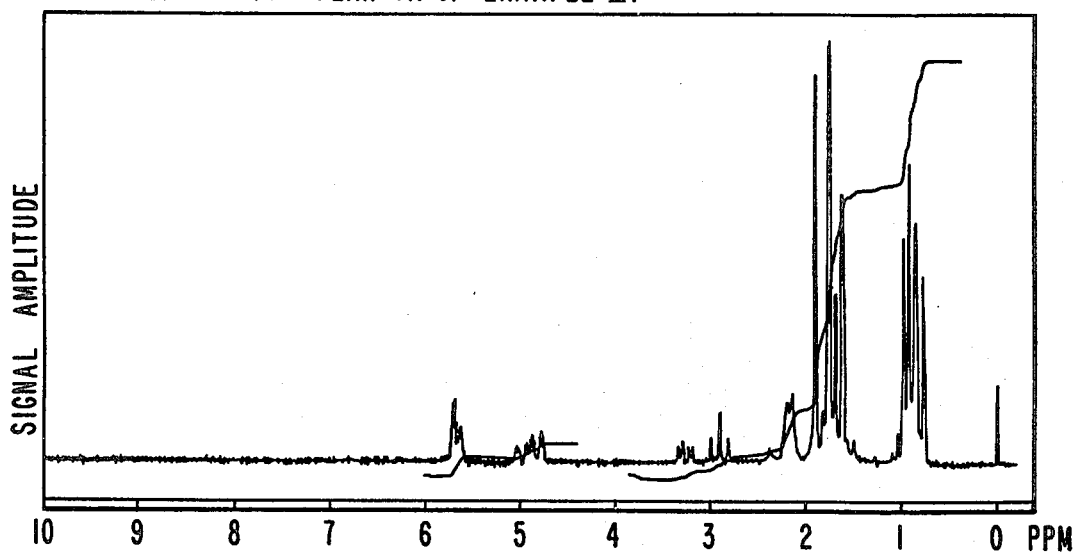

FIG. 12 is the NMR spectrum for Peak 4A of the GLC profile of FIG. 4 which signifies the compound having the structure:

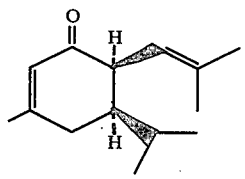

Peak 4A is indicated on FIG. 4 by reference numeral "5".

Figure 13:
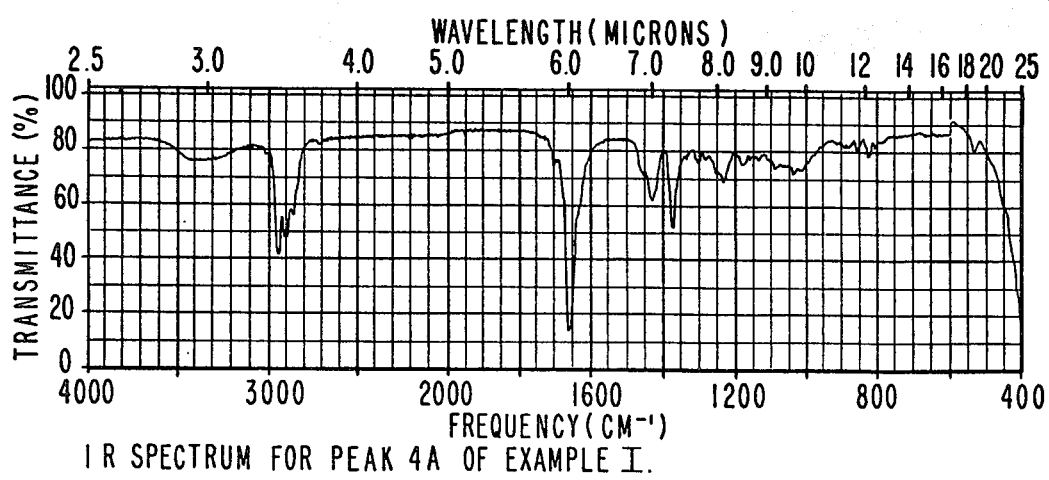

FIG. 13 is the infra-red spectrum for Peak 4A of the GLC profile of FIG. 4 signifying the compound having the structure:

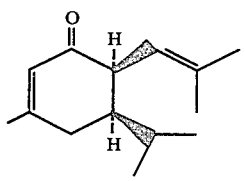

Figure 14:
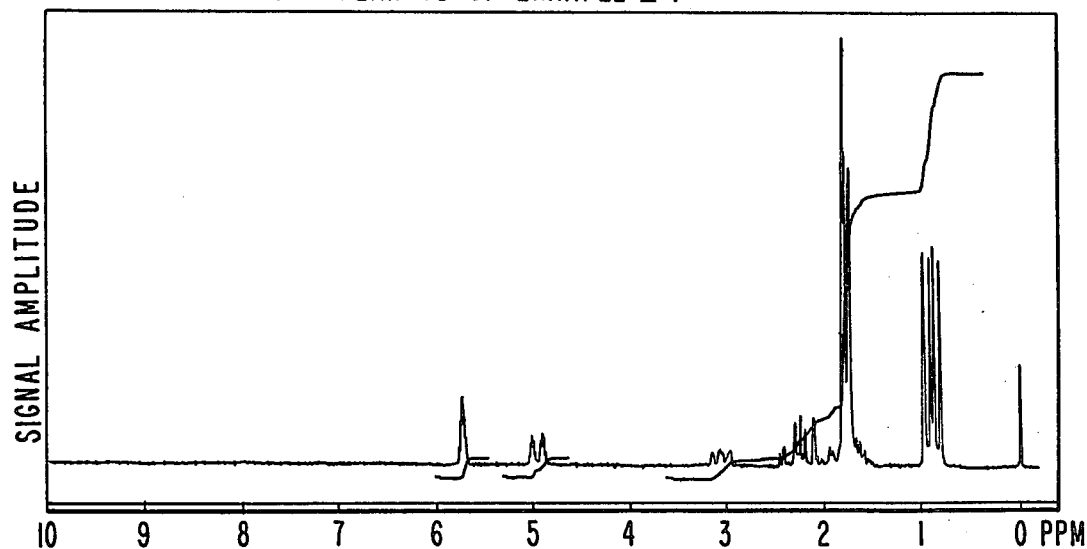

FIG. 14 is the NMR spectrum for Peak 4B of the GLC profile of FIG. 4 signifying the compound having the structure:

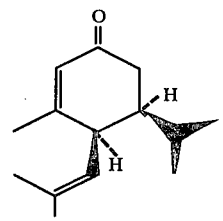

or the compound having the structure:

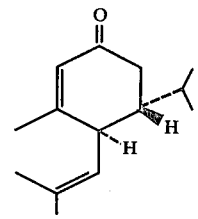

Peak 4B is indicated on FIG. 4 to have the reference numeral "5".

Figure 15:
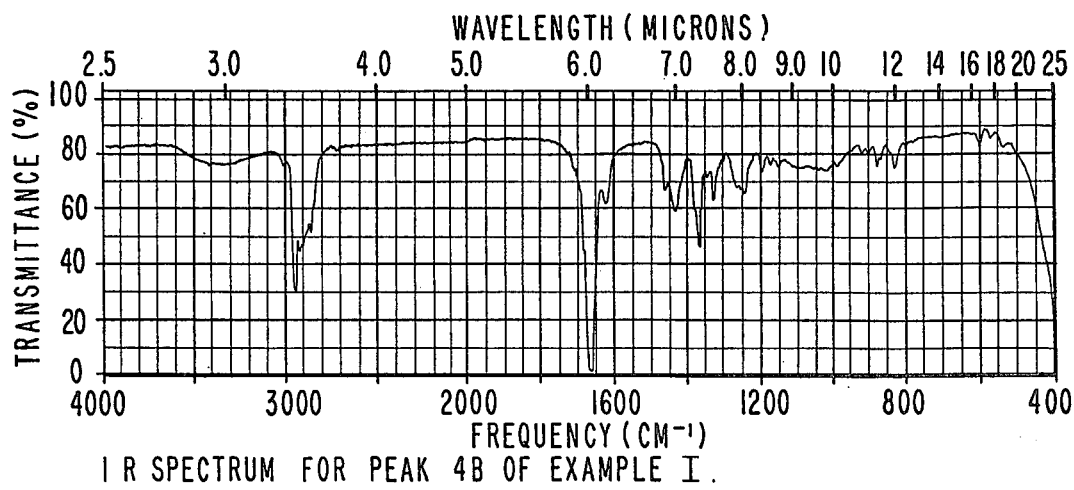

FIG. 15 is the infra-red spectrum for Peak 4B of the GLC profile of FIG. 4 which signifies one of the compounds having the structures:

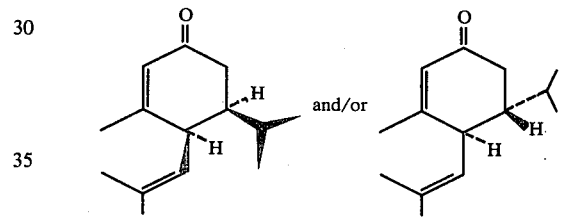

Peak 4B is shown by reference numeral "5" on FIG. 4.

Figure 16:
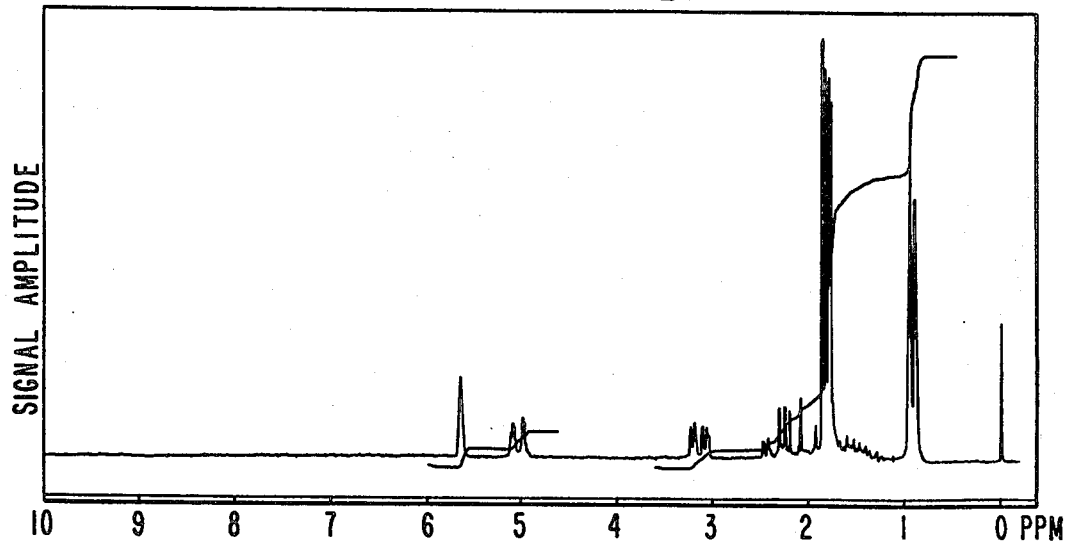

FIG. 16 is the NMR spectrum for Peak 5 of the GLC profile of FIG. 4 signifying the compounds having the structures:

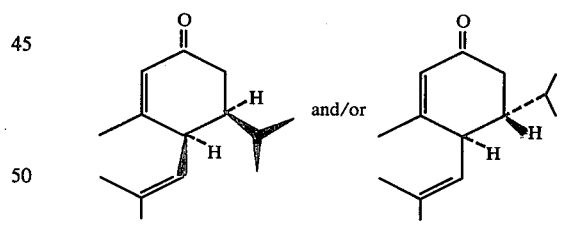

Peak 5 is indicated by the reference numeral "6" on FIG. 4.

Figure 17:
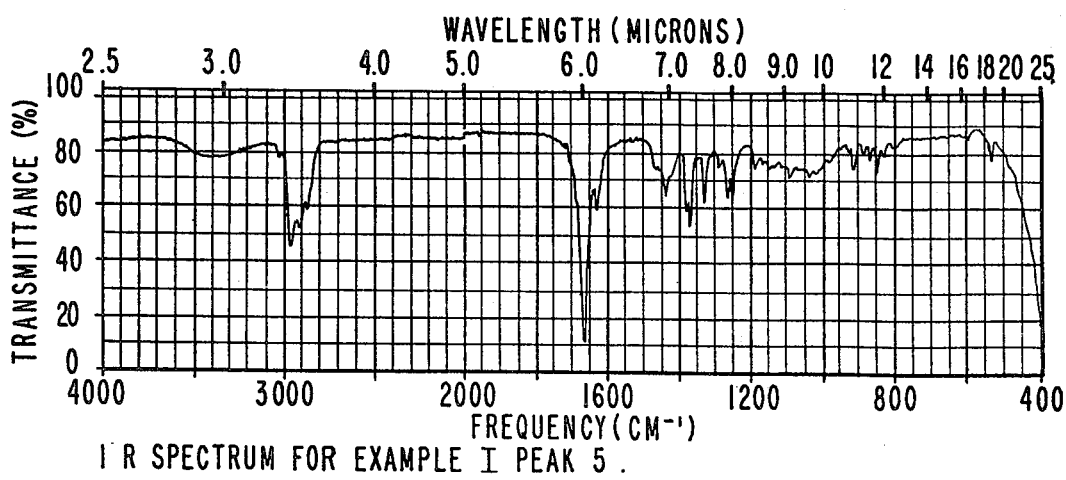

FIG. 17 is the infra-red spectrum for Peak 5 of the GLC profile of FIG. 4 signifying the compounds having the structures:

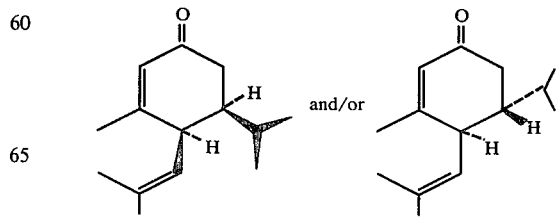

Peak 5 is indicated on FIG. 4 by reference numeral "6".

Figure 18:
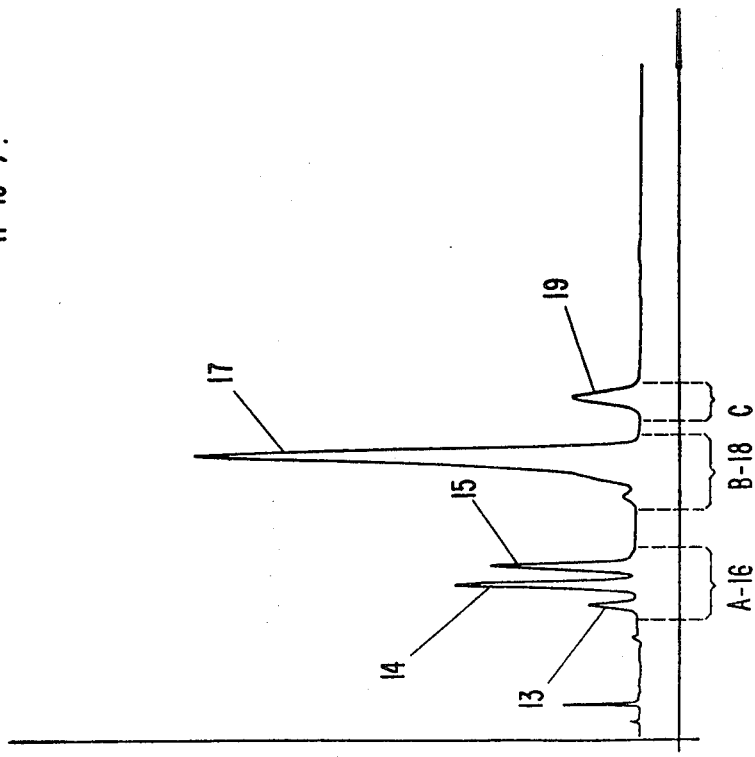

FIG. 18 is the GLC profile for bulked fractions 11–19 of Example I indicating groups of trapped peaks for organoleptic evaluations thusly:
 (i) Group "A" is the combination of Peaks 1, 2 and 3;
 (ii) Group "B" is Peak 4;
 (iii) Group "C" is Peak 5.

Figure 19:
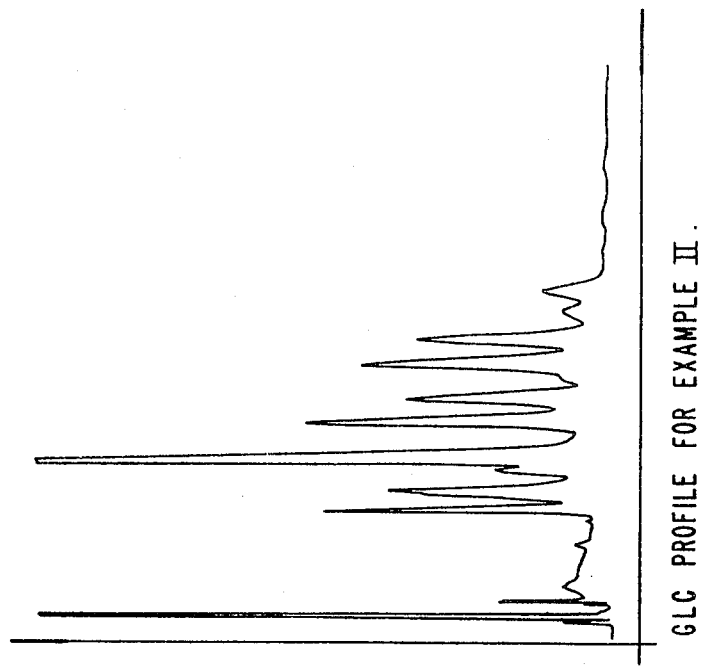

FIG. 19 is the GLC profile for the reaction product of Example II which contains a mixture of compounds defined according to the structure:

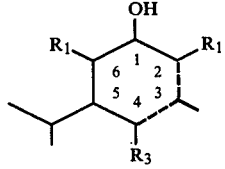

wherein one of the dashed lines represents a carbon-carbon double bond and the other of the dashed lines represents a carbon-carbon single bond; wherein one of $R_1$, $R_2$ and $R_3$ represents 2-methyl-1-propenyl or 2-methyl-1-propylidenyl; and the other of $R_1$, $R_2$ and $R_3$ is hydrogen; with the provisos that:
 (i) when the dashed line at the 3-4 position is a double bond, then $R_3$ is hydrogen or 2-methyl-1-propenyl; and
 (ii) when the dashed line at the 2-3 position is a double bond, then $R_2$ is hydrogen methyl or 2-methyl-1-propenyl.

Figure 20:
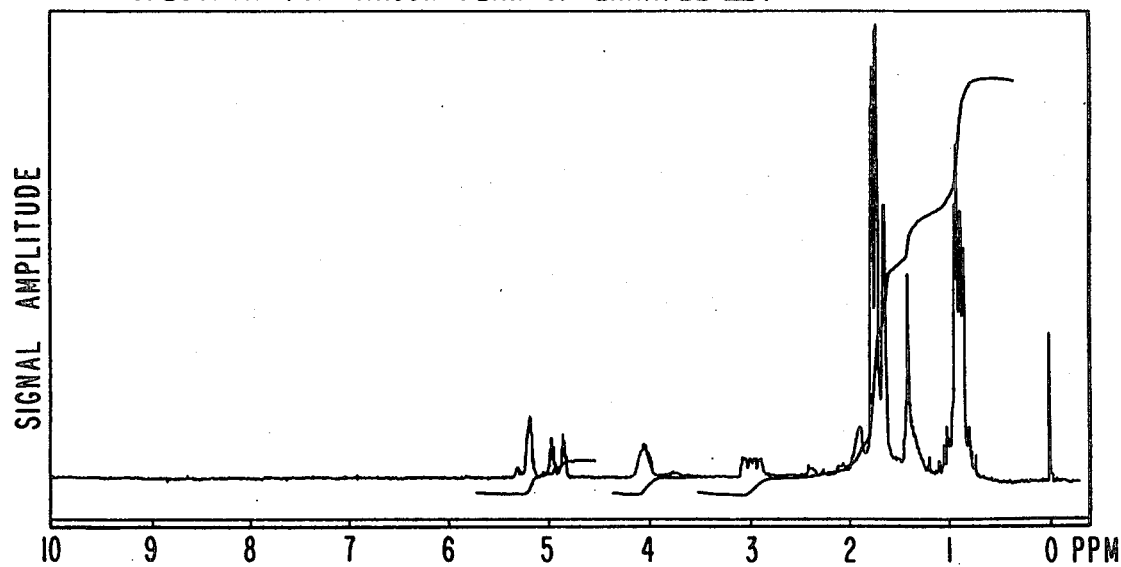

FIG. 20 is the NMR spectrum for the major peak of the GLC profile of FIG. 19 and this major peak has the structure:

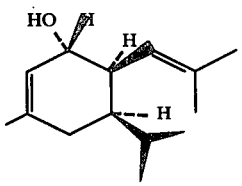

Figure 21:
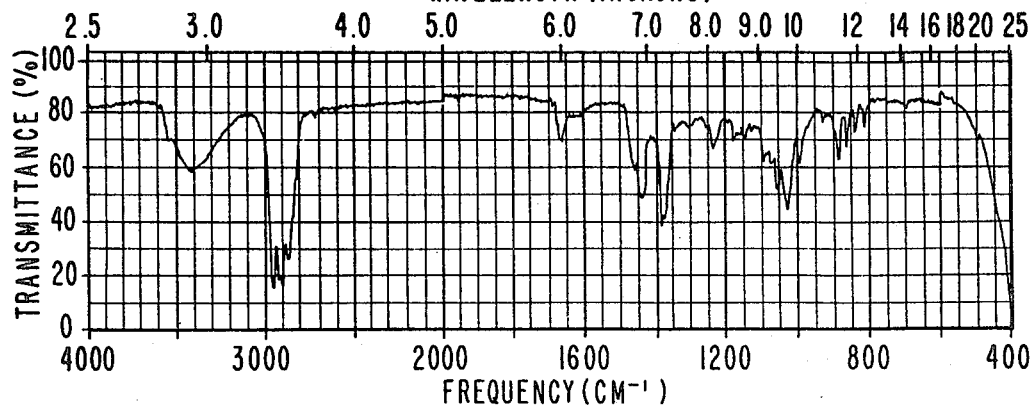

FIG. 21 is the infra-red spectrum for the major peak of the GLC profile of FIG. 19 and this major peak has the structure:

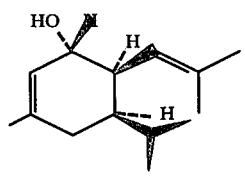

Figure 22:
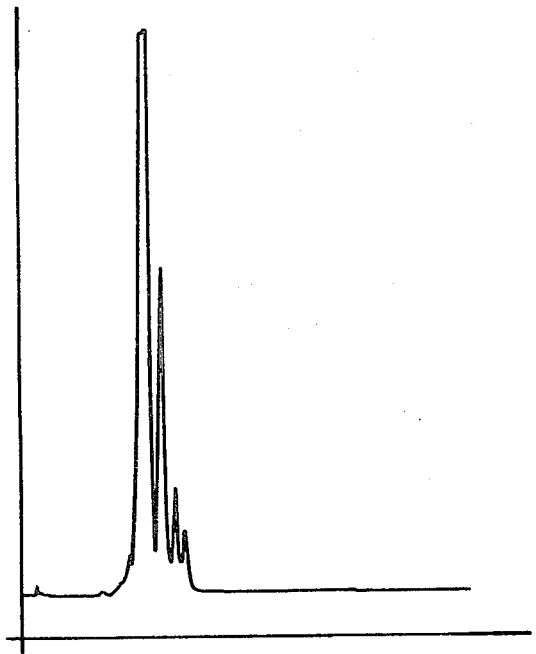

FIG. 22 is the GLC profile for the reaction product of Example III containing a mixture of compounds defined according to the structure:

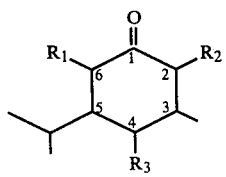

wherein one of $R_1$, $R_2$ and $R_3$ represents 2-methyl-1-propenyl or 2-methyl-1-propylidenyl; and the other of $R_1$, $R_2$ and $R_3$ is hydrogen.

Figure 23:
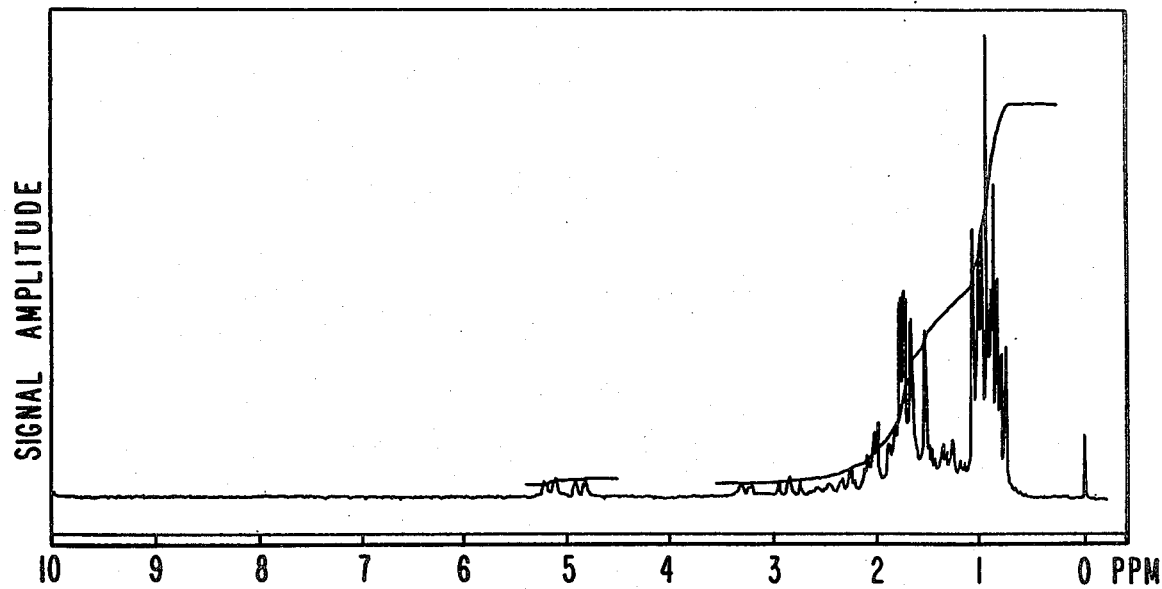

FIG. 23 is the NMR spectrum for the major peak of the GLC profile of FIG. 22 and the major peak has the structure:

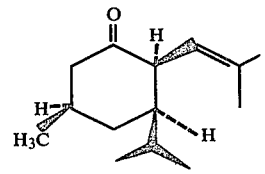

Figure 24:
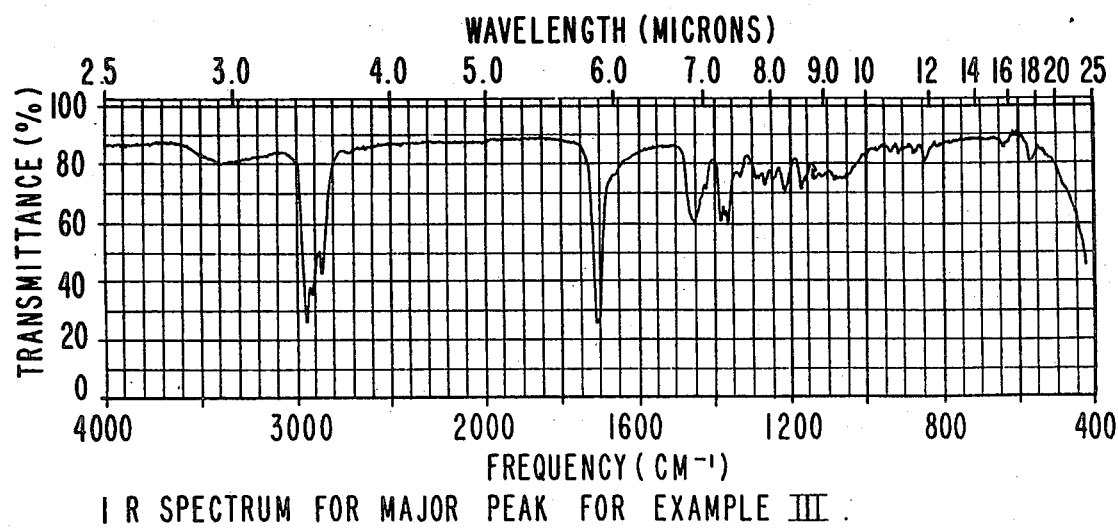

FIG. 24 is the infra-red spectrum for the major peak of the GLC profile of FIG. 22 and the major peak represents the compound having the structure:

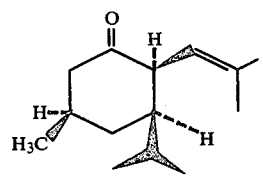

Figure 25:
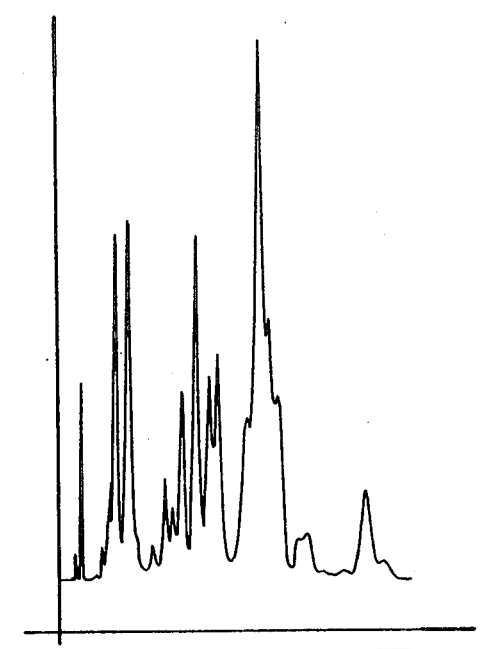

FIG. 25 is the GLC profile for the reaction product of Example IV containing a mixture of compounds defined according to the structure:

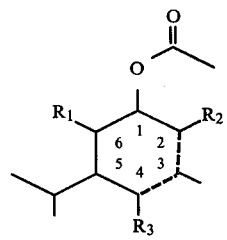

wherein one of the dashed lines represents a carbon-carbon double bond and the other of the dashed lines represents a carbon-carbon single bond; wherein one of $R_1$, $R_2$ and $R_3$ represents 2-methyl-1-propenyl or 2-methyl-1-propylidenyl; and the other of $R_1$, $R_2$ and $R_3$ represent hydrogen; with the provisos that:
 (i) when the dashed line at the 3-4 position is a double bond, then $R_3$ is hydrogen or 2-methyl-1-propenyl; and
 (ii) when the dashed line at the 2-3 position is a double bond, then $R_2$ is hydrogen methyl or 2-methyl-1-propenyl.

Figure 26:
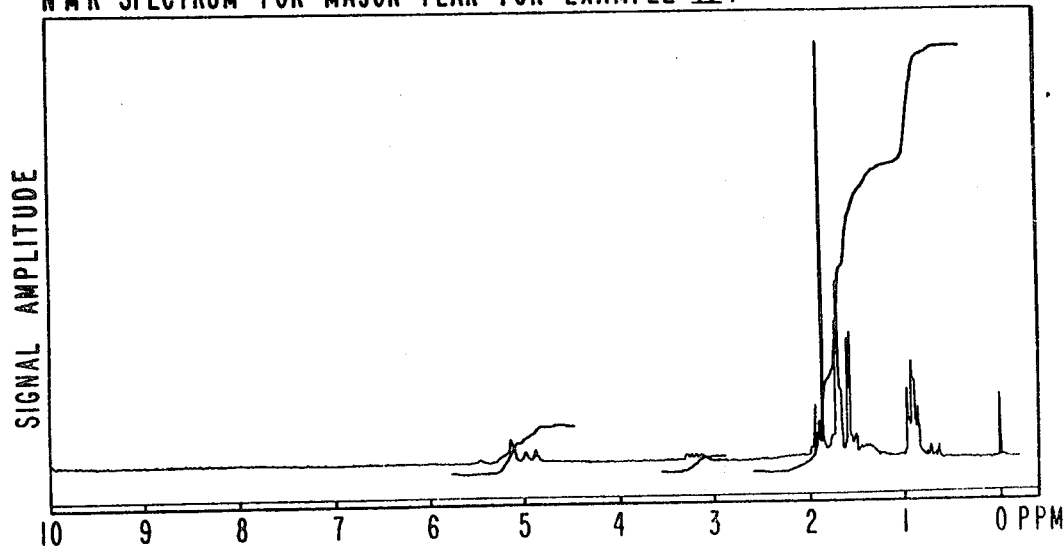

FIG. 26 is the NMR spectrum for the major peak of the GLC profile of FIG. 25 and the major peak is for the compound having the structure:

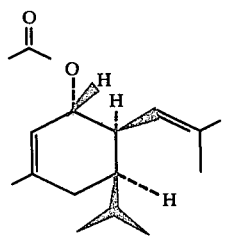

Figure 27:
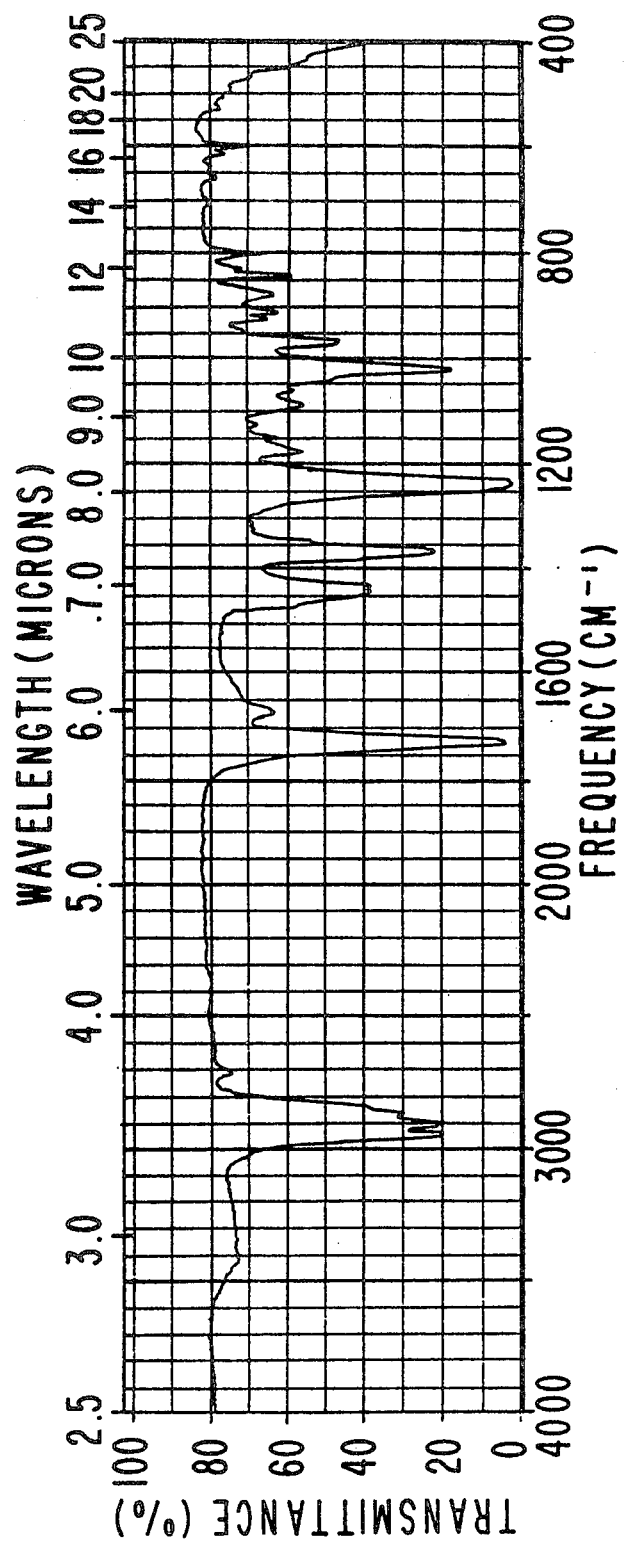

FIG. 27 is the infra-red spectrum for the major peak of the GLC profile of FIG. 25 and is for the compound having the structure:

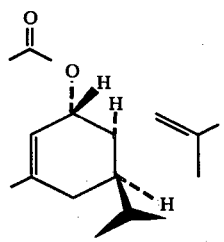

DETAILED DESCRIPTION OF THE DRAWINGS

FIG. 4 is the GLC profile for the crude reaction product produced according to Example I.

The conditions are Carbowax column operated at 200° C., isothermal.

The Peak indicated by the reference numeral "1" is the starting material which is a mixture of compounds defined according to the structure:

wherein in the mixture in each of the molecules one of the dashed lines is a carbon-carbon double bond and the other of the dashed lines is a carbon-carbon single bond and the molecules are different.

The Peaks indicated by reference numerals "2", "3", "4", "5" and "6" represent products produced by means of the dimerization of the compound defined according to the structure:

Thus, the Peak indicated by reference numeral "2" is "Peak 1" which is the compound having the structure:

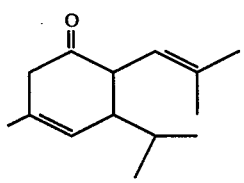

The Peak indicated according to reference numeral "3" is "Peak 2" having the structure:

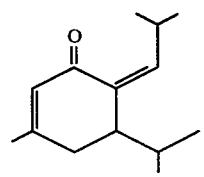

"Peak 3" indicated by reference numeral "4" has the structure:

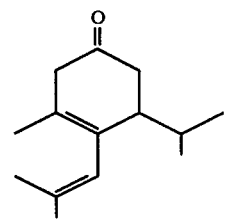

The Peak signified by reference numeral "5" is a combination of Peaks 4A and 4B. Peak 4A is the compound having the structure:

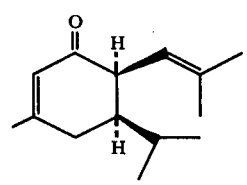

Peak 4B is either the compound having the structure:
Peak 4B is either the compound having the structure:

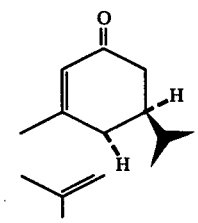

and/or the compound having the structure:

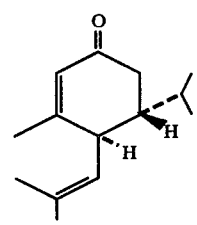

The Peak indicated by reference numeral "6" is Peak 5 which is the compound having the structure:

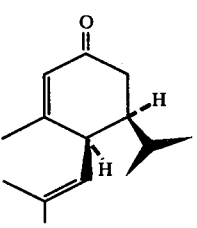

and/or the compound having the structure:

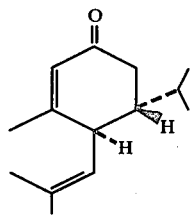

FIG. 5 is the GLC profile for bulked distillation fractions 11-19 of the distillation product of the reaction product of Example I.

The Peak indicated by reference numeral "7" is Peak 1 which is the compound having the structure:

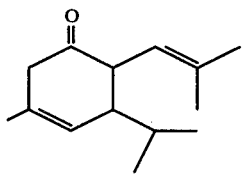

The Peak indicated by reference numeral "8" is Peak 2 having the structure:

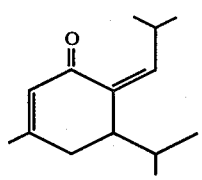

The Peak indicated by reference numeral "9" is Peak 3 having the structure:

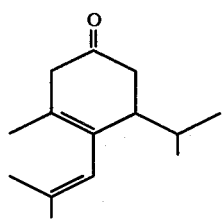

The Peak indicated by reference numeral "10" is Peak 4A having the structure:

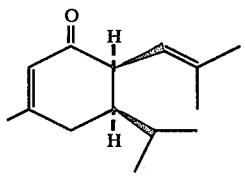

The Peak indicated by reference numeral "11" is Peak 4B having the structure:

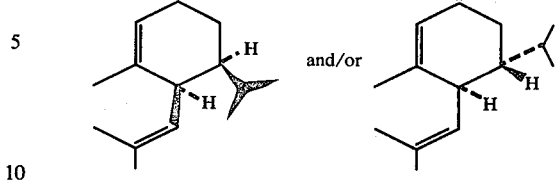

The Peak indicated by reference numeral "12" is Peak 5 having the structure:

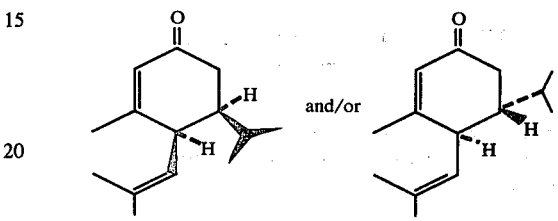

FIG. 18 is the GLC profile for bulked fractions 11-19 of the distillation product of the reaction product of Example I wherein the Peaks are grouped into three groupings:

Group "A" which is Peaks 1, 2 and 3 indicated by reference numerals "13", "14" and "15"

Group "B" which is Peak 4 indicated by reference numeral "17" and

Group "C" which is peak 5 indicated by reference numeral "19".

In Group "A", the peak indicated by reference numeral "13" is Peak 1 having the structure:

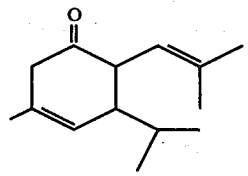

Peak 2 is indicated by reference numeral "14" and has the structure:

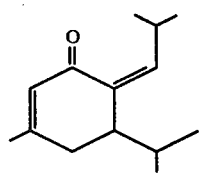

Peak 3 is indicated by reference numeral "15" and has the structure:

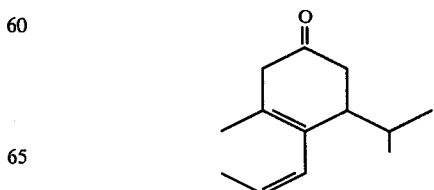

Peak 4 is indicated by reference numerals "17" and "18" and have the structures:

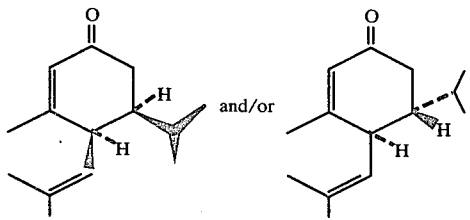

Peak 5 is indicated by reference numeral "19" and has the structure:

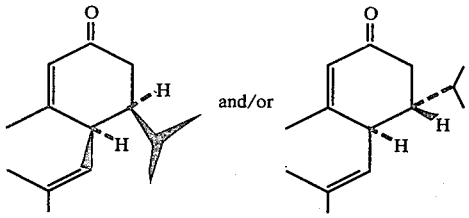

THE INVENTION

It has now been determined that certain substituted methyl isopropyl oxocyclohexane derivatives defined according to the generic structure:

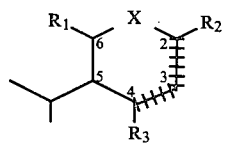

wherein at least one of the lines:

[++++]

is a carbon-carbon single bond and the other of the lines:

[++++]

is either a carbon-carbon single bond or a carbon-carbon double bond; wherein the moiety X represents one of the structures:

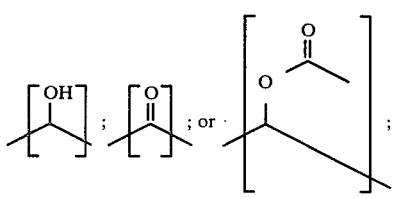

wherein when the moiety X has the structure:

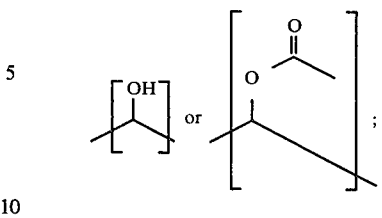

then one of the lines:

[++++]

is a carbon-carbon double bond and the other of the lines:

[++++]

is a carbon-carbon single bond and when the moiety X has the structure:

then both of the lines:

[++++]

represent carbon-carbon single bonds;
wherein one of $R_1$, $R_2$ and $R_3$ represents 2-methyl-1-propenyl or 2-methyl-1-propylidenyl; and the other of $R_1$, $R_2$ and $R_3$ represent hydrogen; with the provisos that:
(i) when the line [++++] at the 3-4 position is a double bond, then $R_3$ is hydrogen or 2-methyl-1-propenyl; and
(ii) when the line [++++] at the 2-3 position is a double bond, then $R_2$ is hydrogen or 2-methyl-1-propenyl, are capable of imparting a variety of fragrances to perfume compositions, colognes and/or perfumed articles.

Briefly, my invention contemplates augmenting or enhancing the fragrances of such consumable materials as perfumes, colognes and perfumed articles by adding thereto a small but effective amount of at least one of the compounds defined according to the structure:

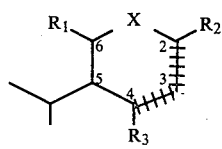

wherein X, $R_1$, $R_2$, $R_3$ and the lines [++++] are defined, supra.

Also contemplated within the scope of my invention are processes for preparing such compounds and the products produced by such processes. These processes involve the dimerization of a mixture of compounds defined according to the structure:

wherein in the mixture one of the dashed lines represents a carbon-carbon double bond and the other of the dashed lines represents a carbon-carbon single bond using a catalyst which is either an alkali metal hydroxide, an alkaline earth metal hydroxide, aluminum chloride, sulfuric acid, or pyrrolidinium acetate in the presence of an inert solvent such as ethanol, methanol, isopropanol, n-propanol, n-hexane, or toluene. The process can be carried out by producing the compound defined according to the structure:

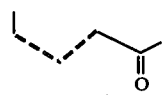

by carrying out the "aldol condensation" of isobutyraldehyde having the structure:

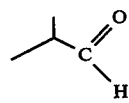

with acetone using the same solvent system as defined above and the same catalyst system as defined above.

The reaction of the isobutyraldehyde with the acetone followed by the dimerization of the resulting compound is shown as follows:

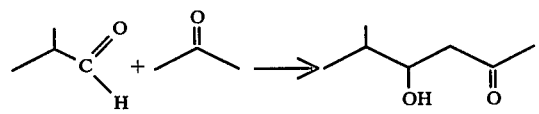

and

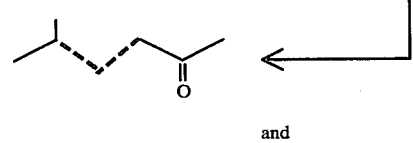

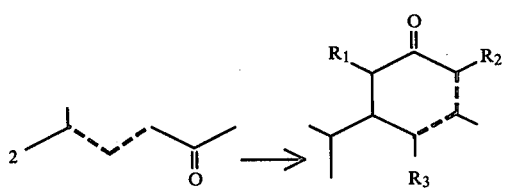

wherein one of the dashed lines represents a carbon-carbon double bond and the other of the dashed lines represents a carbon-carbon single bond and wherein one of $R_1$, $R_2$ and $R_3$ represents 2-methyl-1-propenyl or 2-methyl-1-propylidenyl, and the other of $R_1$, $R_2$ and $R_3$ represent hydrogen; with the provisos that:

(i) when the dashed line at the 3-4 position is a double bond, then $R_3$ is hydrogen or 2-methyl-1-propenyl; and (ii) when the dashed line at the 2-3 position is a double bond, then $R_2$ is hydrogen or 2-methyl-1-propenyl.

The dimerization reaction is carried out at a temperature in the range of from about 25° C. up to about 120° C. at atmospheric pressure in the presence of:

(a) a solvent which can be a hydrocarbon such as n-hexane or toluene; an insert alkanol such as methyl ethanol or isopropyl alcohol; and (b) a catalyst which is either acidic or basic such as an alkali metal hydroxide such as potassium hydroxide or sodium hydroxide; an alkaline earth metal hydroxide such as barium hydroxide; aluminum chloride; or an amphoteric catalyst such as pyrrolidinium acetate defined according to the structure:

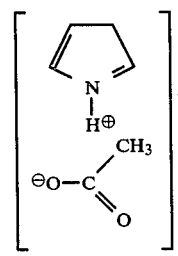

As will be seen by an examination of the GLC profiles in the figures as summarized, supra, the isomer ratios of the reaction product mixture defined according to the structure:

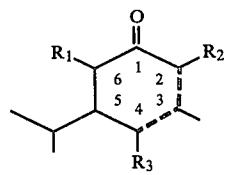

will vary and depend upon the following reaction variables:

(a) temperature of reaction;
(b) time or reaction;
(c) nature of catalyst;
(d) concentration of catalyst;
(e) nature of solvent;
(f) concentration of reactant in solvent;
(g) ratio of catalyst to reactant.

When carrying out the reaction between the isobutyraldehyde and acetone in situ, the mole ratio of isobutyraldehyde:acetone may vary from 1.5:0.5 up to 0.5:1.5 isobutyraldehyde:acetone. The reaction temperature range may vary from about 25° C. up to about 120° C. and is preferably the temperature at which the reaction mass will reflux at atmospheric pressure. Thus, when carrying out the reaction using a methyl alcohol catalyst wherein the reactant concentration is 4 kg. per liter using methanol, the reaction temperature is maintained at 50°–52° C.

The concentration of catalyst in the reaction mass may vary from about 50 grams per liter up to about 400 grams per liter. The nature of the solvent may vary as set forth above with the preferred solvents being methanol, ethanol and isopropyl alcohol. The nature of the catalyst may vary as set forth above with the preferred catalysts being sodium hydroxide, potassium hydroxide and barium hydroxide.

If desired the substituted methyl isopropyl cyclohexenones defined according to the generic structure:

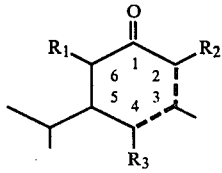

may be separated and obtained in pure form or in substantially pure form by conventional purification techniques. Thus, the products can be purified and/or isolated by distillation, extraction, crystallization, preparative chromatographic techniques (column chromatography and vapor phase chromatography) and the like. It has been found desirable to purify the substituted methyl isopropyl cyclohexenone derivatives having the structure:

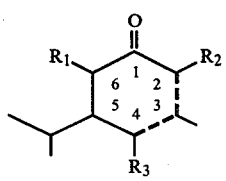

of my invention by fractional fractional distillation in vacuo, prior to carrying out the reduction reactions to form the compounds defined according to the structure:

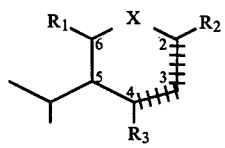

more specifically the compounds having the structures:

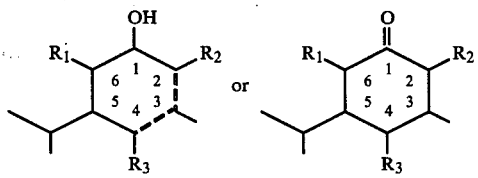

wherein the dashed lines, X, $R_1$, $R_2$ and $R_3$ are defined, supra and the lines [++++] are also defined supra.

The reduction reaction for the reduction of the compounds defined according to the generic structure:

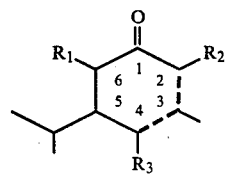

to form the compounds defined according to the generic structure:

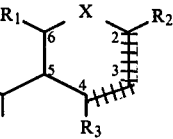

can be carried out using either an alkali metal borohydride such as sodium borohydride, potassium borohydride or lithium borohydride or can be carried out using hydrogen and a catalyst such as palladium on carbon (3%, 5%, 7%, or 10% palladium on carbon); palladium on calcium carbonate (3%, 5%, or 10% palladium on calcium carbonate) or palladium on barium sulfate (5% or 10% palladium on barium sulfate).

When carrying the reaction using the alkali metal borohydride, the compounds formed will be the cyclohexenol derivatives defined according to the structure:

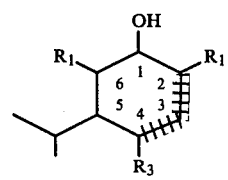

according to the reaction:

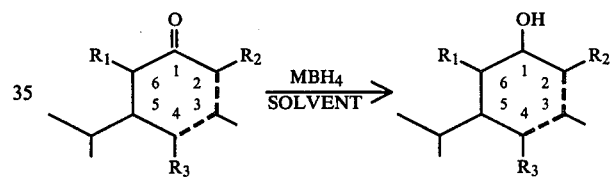

wherein the dashed lines and $R_1$, $R_2$ and $R_3$ are defined, supra. The reaction is carried out in the presence of a solvent which is inert to the reaction mass such as methanol, ethanol, isopropyl alcohol or n-propanol. The alkali metal borohydride usable is sodium borohydride, potassium borohydride or lithium borohydride with sodium borohydride being preferred because of its availability and low cost. The concentration of alkali metal borohydride in the reaction mass may vary from about 20 grams per liter of reaction mass up to about 50 grams per liter of reaction mass. The concentration of ketone mixture or ketone product defined according to the structure:

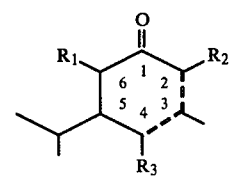

may vary from 200 grams per liter up to about 800 grams per liter with a preferred concentration of ketone being about 550-650 grams per liter. The reaction temperature is in the range of 40°-70° C. with a preferred reaction temperature of 45°-55° C. at atmospheric pressure. Utilization of pressures greater than atmospheric will permit an increase in reaction temperature and a shorter reaction times but no advantage in yield or conversion exists using such higher pressures.

In carrying out the reduction of the ketones having the structure:

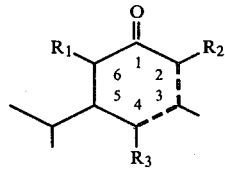

to form the cyclohexanone derivative defined according to the structure:

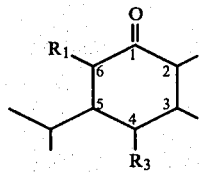

hydrogen is used as the reducing agent using a catalyst such as palladium, palladium on a carbon support, palladium on a calcium carbonate support or palladium on a barium sulfate support. The most preferred catalyst is 5% palladium on carbon. The hydrogen pressure may vary from 50 psig up to 10 atmospheres with a preferred hydrogen pressure of 100 psig. The mole ratio of hydrogen:ketone reactant defined according to the structure:

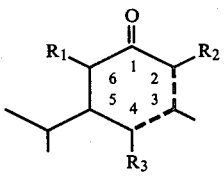

is in the range of from 1:1 hydrogen:ketone up to about 3:1 hydrogen:ketone with a preferred mole ratio of 1:1 hydrogen:ketone reactant. The reaction is carried out in an inert solvent such as isopropyl alcohol, n-propyl alcohol, methanol or ethanol. The temperature of reaction according to the reaction scheme:

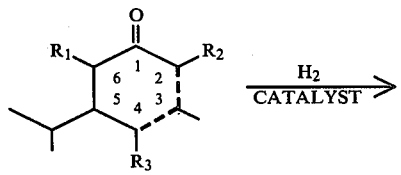

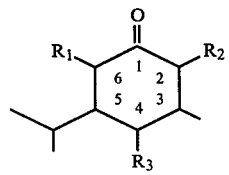

may vary from about 20° C. up to about 100° C. Higher temperatures of reaction do not give rise to higher yields but instead give rise to an increased concentration of undesired by-product which are difficult to separate from the reaction product defined according to the structure:

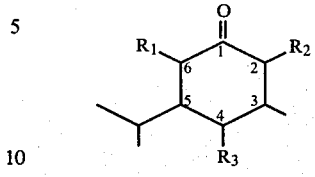

The formation of the compound or mixture of compounds of my invention defined according to the structure:

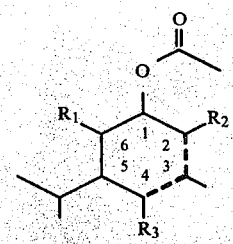

wherein $R_1$, $R_2$, $R_3$ and the dashed lines are defined, supra is carried out according to the reaction:

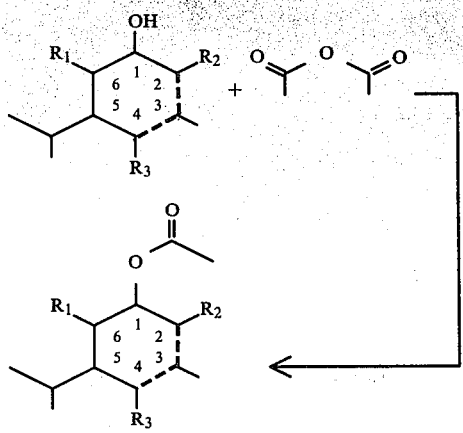

wherein acetic anhydride is reacted with the cyclohexenol derivative(s) produced as set forth, supra. THe cyclohexenol are first separated from the reaction mass as by fractional distillation in vacuo and then reacted with the acetic anhydride.

The reaction temperature is preferably in the range of from about 90° C. up to about 120° C. and is preferably at 100° C. The mole ratio of acetic anhydride:alcohol reactant may vary from about 1:0.5 up to about 2:1 alcohol:acetic anhydride. The time of reaction may vary from about one hour up to about three hours depending upon the temperature of reaction. Higher pressures of reaction (greater than atmospheric) give rise to lower temperatures of reaction and consequently shorter times of reaction. However it is most preferred and convenient to carry out the reaction at a 100° C. and one atmosphere pressure. At the end of the reaction the reaction mass is washed and neutralized with a weak base such as sodium carbonate. Subsequently the reaction mass is washed with water, dried and distilled on a fractional distillation in vacuo to yield the desired acetate which then has uses in perfumery, colognes and perfumed articles as set forth, infra.

In each of the foregoing cases the reaction product after the reaction may be "worked up" whereby various groups of reaction products or individual reaction products may be obtained in pure form or in admixture by conventional purification techniques. Thus, the products can be purified, isolated or formed into desired mixtures by means of fractional distillation, extraction, crystallization, preparative chromatographic techniques (column chromatography and vapor phase chromatography) and the like. It has been found most desirable to purify the substituted methyl isopropyl oxocyclohexane derivatives of my invention by fractional distillation in vacuo.

Examples of the compounds produced according to the processes of my invention and the organoleptic properties thereof are as follows:

TABLE I

| Structure Defining Mixture Produced | Perfume Properties |
| --- | --- |
| Mixture of compounds defined according to the structure: 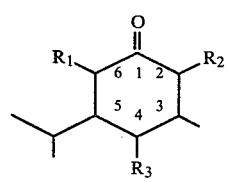 produced according to Example III, infra. | A herbaceous, woody, earthy, camphoraceous tobacco resin-like guiacwood-like, cardamom-like; jute-like; spicy, honey and sweaty aroma profile. |
| Mixture of compounds defined according to the structure: 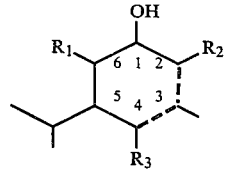 produced according to Example II. | A woody, fruity ionone-like, smokey, rosey, vetiver-like, camphoraceous, fruity and musky aroma profile. |
| Mixture of compounds defined according to the structure: 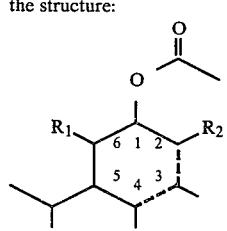 produced according to Example IV, infra. | A woody, ionone-like aroma profile. |

The substituted methyl isopropyl oxocyclohexane derivatives of my invention can be used alone or in combination to contribute herbaceous, woody, earthy, camphoraceous, tobacco resin-like, guiacwood, cardamom, jute-like, spicy, honey, sweaty, ionone-like, smokey, rosey, vetiver-like, fruity and musky aroma nuances to perfumes, perfumed articles and colognes.

As olfactory agents the substituted methyl isopropyl oxocyclohexane derivatives of my invention can be formulated into or used as components of a "perfume composition" or can be used as components of a "perfumed article" or the perfume composition may be added to "perfumed articles".

The term "perfume composition" is used herein to meet a mixture of organic compounds including for example alcohols (other than the alcohols of my invention), aldehydes, ketones (other than the ketones of my invention), nitriles ethers, lactones, natural essential oils, synthetic essential oils and frequently hydro carbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, the individual component will contribute its particular olfactory characteristics, but the overall effect of the perfume composition will be the sum total of the effects of each of the ingredients and possibly even more than the sum total of each of the effects of each of the ingredients if there exists synergism amongst the ingredients. Thus, the individual compounds of this invention or mixtures thereof can be used to alter, augment or enhance the aroma characteristics of a perfume composition, for example, by highlighting or moderating the olfactory reaction contributed by another ingredient in the composition.

The amount of the substituted methyl isopropyl oxocyclohexane derivatives of this invention which will be effective in perfume compositions depends on many factors, including the other ingredients, their amounts and the effects which are desired. It has been found that perfume compositions containing as little as 0.05% of the substituted methyl isopropyl oxocyclohexane derivatives of this invention, or even less, can be used to impart an interesting herbaceous, woody, earthy, camphoraceous, tobacco resin-like, quiacwood-like, cardamom-like, jute-like, spicy, honey, sweaty, ionone-like, smokey, rosey, vetiver-like, fruity and musky aroma nuances to soaps, liquid and solid cationic, anionic, nonionic and zwitterionic detergents, cosmetic powders, liquid and solid fabric softeners, fabric softeners articles, optical brightener compositions and other products. The amount employed can range up to 50% or higher and will depend on consideration of cost, nature of the end product and the effect desired on the finished product and the particular fragrance sought.

The substituted methyl isopropyl oxocyclohexane derivatives of this invention can be used alone or in a perfume composition as an olfactory component in detergents and soaps, space odorants and deodorants; perfumes; colognes, toilet waters; bath salts; hair preparations such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of one or more of the substituted methyl isopropyl oxocyclohexane derivatives of my invention will suffice to impart an interesting herbaceous, woody, earthy, camphoraceous, tobacco resin-like, guiacwood, cardamom, jute-like, spicy, honey, sweaty, ionone-like, smokey, rosey, vetiver-like, fruity and musky aroma nuances. Generally, no more than 0.5% (by weight of the perfumed article) is required. Thus, the range of use of the substituted methyl isopropyl oxocyclohexane derivatives of my invention in perfumed articles is 0.01% up to 0.5% and the use in perfume compositions per se is from 0.05% up to 50% of the substituted methyl isopropyl oxocyclohexane derivatives of my invention.

In addition, the perfume compositions can contain a vehicle or carrier for the substituted methyl isopropyl oxocyclohexane derivatives of my invention taken alone or taken together with other ingredients. The vehicle can be a liquid such as an alcohol such as ethanol, a glycol such as propylene glycol or the like. The carrier can be an absorbent solid such as a gum (e.g., gum arabic or guar gum or xanthan gum) or components for encapsulating the composition such as gelatin (as by coacervation) which can be used to form a capsule wall surrounding the perfume oil, or a urea formaldehyde resin which is formed by polymerization to form a capsule wall surrounding the perfume oil.

It will thus be apparent that the substituted methyl isopropyl oxocyclohexane derivatives of my invention can be used to alter, modify, augment or enhance sensory properties, particularly organoleptic properties such as fragrances of a wide variety of consumable materials.

The following Examples A and I serves to illustrate methods for producing precursors which are used in producing the products of my invention. The following Examples II–IV inclusive, serve to illustrate the processes for carrying out the chemical syntheses of the products of my invention. The following Examples V et seq. set forth the uses of the products of Examples II–IV of my invention. The invention is to be considered restricted to these examples only as indicated in the appended claims.

All parts and percentages given herein are by weight unless otherwise specified.

EXAMPLE A

PREPARATION OF 5-METHYL-HEXANE-2-ONE MIXTURE

Reaction:

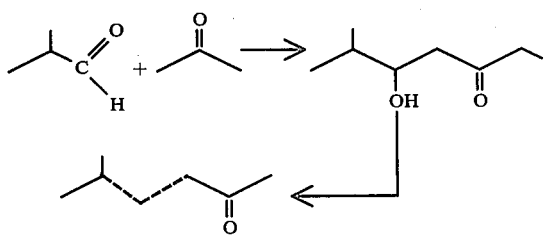

Into a 5 liter reaction flask equipped with stirrer, thermometer, condenser, addition funnel and heating mantle and fitted with a Soxhlet apparatus containing a thimble filled with barium hydroxide (200 grams) is placed a mixture of 1.5 kg of isobutyraldehyde and 1.4 kg of acetone.

The reaction mass is refluxed and the resultant 5-methylhexene-2-one mixture is collected in the reaction flask for a period of 4 hours.

At the end of the 4 hour period, the reaction mass is stripped of excess reactants and 2.3 kg of 5-methyl-hexene-2-one compounds are collected via distillation at a temperature of 74° C. and a pressure of 0.8 mm/Hg pressure.

Figure 1:
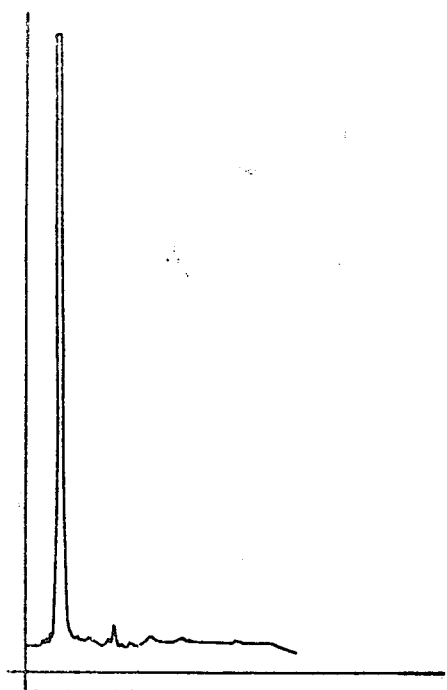
FIG. 1 is the GLC profile for the reaction product of Example A wherein the mixture defined according to the structure.

FIG. 1 is the GLC profile of the reaction product (conditions: Carbowax column operated at 200° C. isothermal).

FIG. 2 is the NMR spectrum for the reaction product collected via distillation at the temperature of 74° C. and 0.8 mm/Hg pressure.

FIG. 3 is the infra-red spectrum for the resulting product which is a mixture of compounds defined according to the structure:

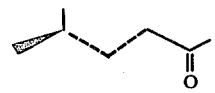

wherein in the mixture, in each of the molecules, one of the dashed lines is a carbon-carbon double bond and the other of the dashed lines is a carbon-carbon single bond and the molecules of the mixture are different.

EXAMPLE I

DIMERIZATION OF 5-METHYL-HEXENE-2-ONE MIXTURE

Reaction:

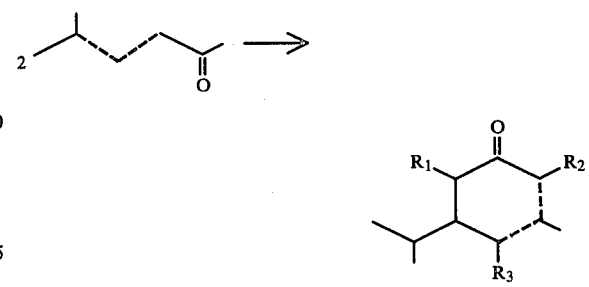

wherein one of $R_1$, $R_2$ or $R_3$ is 2-methyl-1-propenyl having the structure:

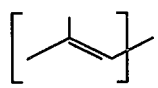

or 2-methyl-1-propylidenyl having the structure:

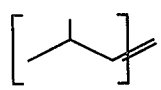

and the other two of $R_1$, $R_2$ or $R_3$ is hydrogen; and wherein in the mixture, in each of the molecules of the mixture, one of the dashed lines is a carbon-carbon double bond and the other of the dashed lines is a carbon-carbon single bond and wherein the molecules of the mixture are represented thusly:

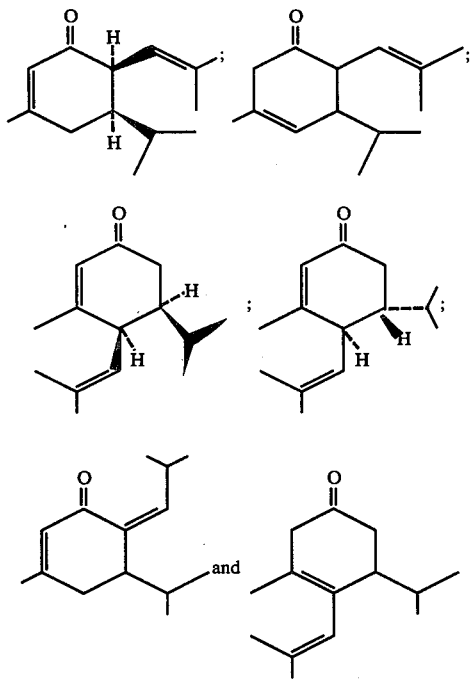

Into a 5 liter reaction flask equipped with stirrer, thermometer, condenser, addition funnel, heating mantle, cooling bath and Therm-o-watch apparatus is placed 100 grams of potassium hydroxide. 500 ml of methanol is placed in an addition funnel. Over a period of 10 minutes, the methanol is added to the KOH. After the methanol is mixed with the KOH, the resulting mixture is heated to 50° C. and over a period of 1 hour, the 5-methyl-hexene-2-one mixture (2 kg) produced according to Example A (boiling point 74° C. at 0.8 mm/Hg pressure) is added to the reaction mass while maintaining the reaction mass at 50°-55° C. At the end of the addition, the reaction mass is stirred for a period of 1.5 hours at 50°-51° C. The reaction mass is then added to two liters of water and the resulting organic layer is washed with two liters of water to a pH of 7. The organic layer is then distilled on a 24" Goodloe column to yield 917.2 grams of product and the fractions resulting from this distillation are as follows:

| Fraction Number | Vapor Temp. (°C.) | Liquid Temp. (°C.) | Pressure mm/Hg | Reflux Ratio | Weight of Fraction (grams) |
|---|---|---|---|---|---|
| 1 | 60/85 | 147/143 | 0.4/.25 | 9:1 | 47.2 |
| 2 | 92 | 140 | 0.25 | 9:1 | 44.5 |
| 3 | 98 | 140 | 0.30 | 9:1 | 36.3 |
| 4 | 84 | 139 | 0.22 | 9:1 | 44.7 |
| 5 | 88 | 141 | 0.40 | 9:1 | 39.9 |
| 6 | 88 | 142 | 0.40 | 9:1 | 42.0 |
| 7 | 88/95 | 140/141 | 0.4/0.4 | 9:1 | 41.0 |
| 8 | 104 | 145 | 0.7 | 9:1 | 45.7 |
| 9 | 101 | 148 | 0.6 | 9:1 | 43.1 |
| 10 | 103 | 148 | 0.5 | 9:1 | 39.9 |
| 11 | 102 | 148 | 0.4 | 9:1 | 48.2 |
| 12 | 102 | 148 | 0.4 | 9:1 | 49.8 |
| 13 | 103 | 149 | 0.4 | 9:1 | 41.2 |
| 14 | 104 | 150 | 0.4 | 9:1 | 24.8 |
| 15 | 103 | 150 | 0.4 | 9:1 | 47.0 |
| 16 | 92/100 | 145/147 | 0.4/0.4 | 2:1 | 36.4 |
| 17 | 93 | 142 | 0.4 | 2:1 | 48.7 |
| 18 | 93 | 143 | 0.4 | 2:1 | 41.6 |
| 19 | 93 | 146 | 0.4 | 2:1 | 45.1 |
| 20 | 93 | 150 | 0.4 | 2:1 | 38.1 |

| Fraction Number | Vapor Temp. (°C.) | Liquid Temp. (°C.) | Pressure mm/Hg | Reflux Ratio | Weight of Fraction (grams) |
|---|---|---|---|---|---|
| 21 | 95 | 195 | 0.5 | 2:1 | 39.6 |

Fractions 7-22 are bulked for the purposes of organoleptic evaluation. From an aroma standpoint, bulked fractions 7-22 have a peppery, guiacwood-like, vetiver-like, sandalwood-like aroma with a sauge sclaree top-note and a musky undertone.

FIG. 4 is the GLC profile for the crude reaction product (GLC conditions: Carbowax column operated at 200° C. isothermal).

The Peak on the GLC profile indicated by the reference numeral "1" represents the starting material having the structure:

a mixture, wherein in the mixture in one of the molecules one of the dashed lines is a carbon-carbon double bond and the other of the dashed lines is a carbon-carbon single bond and in the other of the molecules, the other of the dashed lines is a carbon-carbon double bond.

The Peak indicated by the reference numeral "2", Peak 1, has the structure:

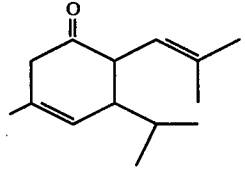

The Peak indicated by the reference numeral "3", Peak 2, has the structure:

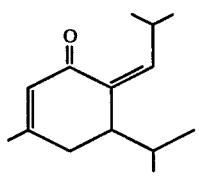

The Peak indicated by the reference numeral "4", Peak 3, has the structure:

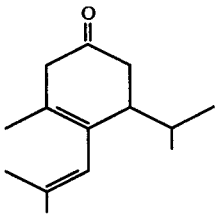

The Group of Peaks indicated by the reference numeral "5" is a mixture of Peaks 4A and 4B. Peak 4A has the structure:

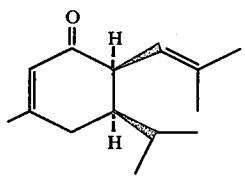

Peak 4B has the structure:

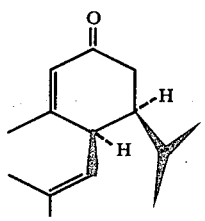 and/or 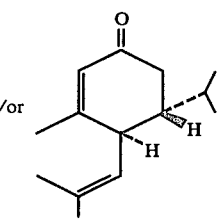

The Peak indicated by reference numeral "6" is Peak 5 and it has the structure:

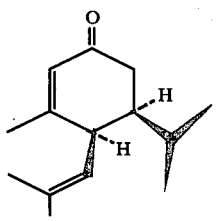 and/or 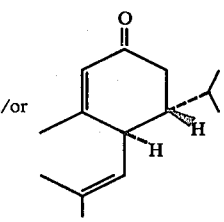

FIG. 5 is the GLC profile for the bulked distillation fractions 11–19 of the foregoing distillation of the foregoing reaction product.

The Peak indicated by reference numeral "7" is Peak 1 having the structure:

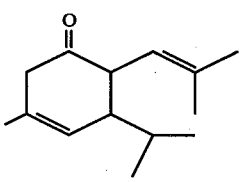

The Peak indicated by reference numeral "8" is Peak 2 having the structure:

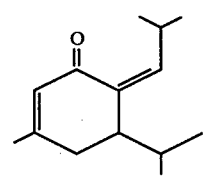

The Peak indicated by reference numeral "9" is Peak 3 having the structure:

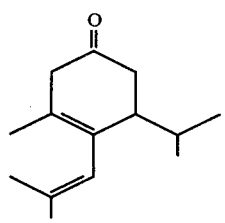

The Peak indicated by reference numeral "10" is Peak 4A having the structure:

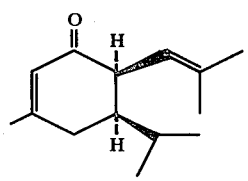

The Peak indicated by reference numeral "11" is Peak 4B having the structure:

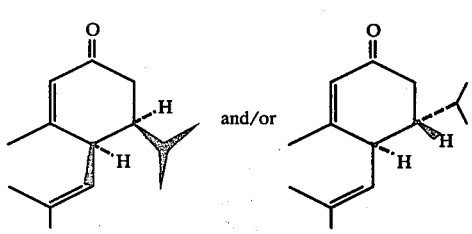

The Peak indicated by reference numeral "12" is Peak 5 having the structure:

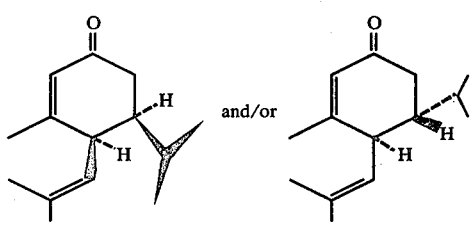

FIG. 6 is the NMR spectrum for Peak 1 having the structure:

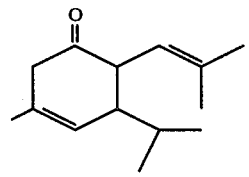

FIG. 7 is the IR spectrum for Peak 1 of the foregoing GLC profile having the structure:

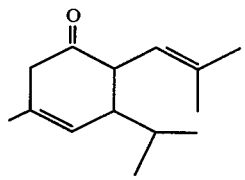

FIG. 8 is the NMR spectrum for Peak 2 of the foregoing GLC profile having the structure:

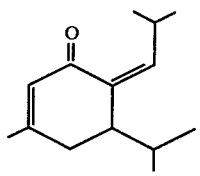

FIG. 9 is the infra-red spectrum for Peak 2 of the foregoing GLC profile having the structure:

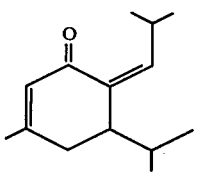

FIG. 10 is the NMR spectrum for Peak 3 of the foregoing GLC profile having the structure:

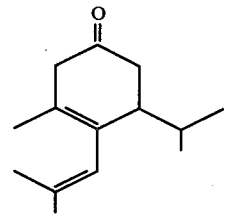

FIG. 11 is the infra-red spectrum for Peak 3 of the foregoing GLC profile having the structure:

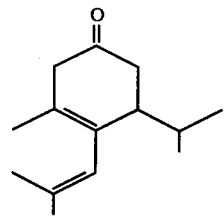

FIG. 12 is the NMR spectrum for Peak 4A of the foregoing GLC profile having the structure:

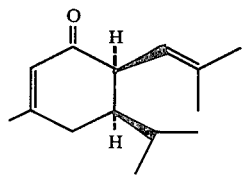

FIG. 13 is the infra-red spectrum for Peak 4A of the foregoing GLC profile having the structure:

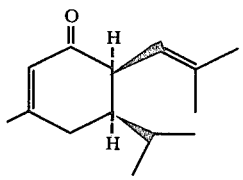

FIG. 14 is the NMR spectrum for Peak 4B of the foregoing GLC profile having the structure:

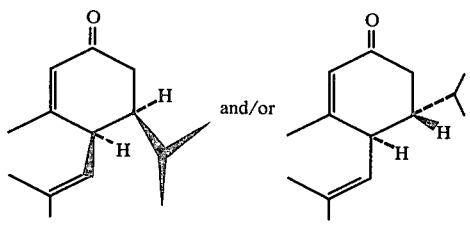

FIG. 15 is the infra-red spectrum for Peak 4B of the foregoing GLC profile having the structure:

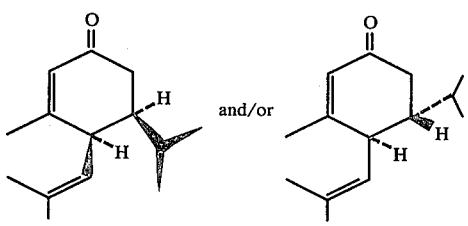

FIG. 16 is the NMR spectrum for Peak 5 of the foregoing GLC profile having the structure:

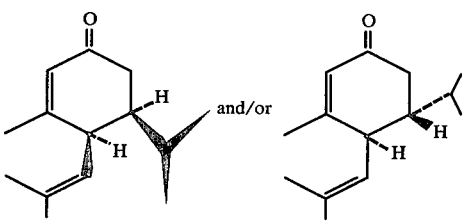

FIG. 17 is the infra-red spectrum for Peak 5 of the foregoing GLC profile having the structure:

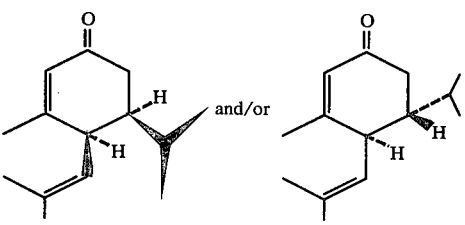

FIG. 18 is the GLC profile for bulked fractions 11–19.

The Peaks of the GLC profile are grouped as follows: Group "A" is a mixture of Peaks 1, 2 and 3. Group "A" has a sweaty, burnt grass aroma.

Group "B" is a mixture of Peaks 4A and 4B. Group "B" has an intense peppery, guiacwood, vetiver, sandalwood-like aroma with a sauge sclaree topnote and a musky undertone.

Group "C" is Peak 5. Group "C" has a green, vetiver aroma.

EXAMPLE II

PREPARATION OF REDUCTION OF METHYL ISOPROPYL CYCLOHEXENONE MIXTURE USING ALKALI METAL BOROHYDRIDES

Reaction:

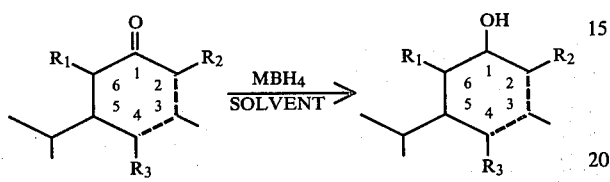

(wherein the dashed lines and $R_1$, $R_2$ and $R_3$ are defined, supra.)

Into a 3 liter reaction flask equipped with stirrer, thermometer, reflux condenser, dropping funnel, nitrogen blanket apparatus, cooling bath and heating mantle are placed 39 grams of sodium borohydride and 300 ml of anhydrous isopropyl alcohol. Into the dropping funnel is placed 500 grams of the bulked distillation product, fractions 11-19 of the ketone mixture produced according to Example I, supra defined according to the structure:

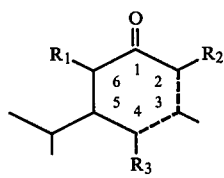

While the temperature is being raised from 25°-50° C., and over a period of one hour the ketone mixture of bulked fractions 11-19 of Example I is added to the sodium borohydride-isopropyl alcohol mixture. At the end of the addition the reaction mass is maintained at 45°-50° C. with stirring for a period of three hours.

The reaction mass is then added to 1 liter of 10% hydrochloric acid and the organic layer is washed with one liter of a 10% sodium chloride solution.

The reaction mass is then distilled yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 85/90 | 115/118 | 0.6 | 11.7 |
| 2 | 90 | 117 | 0.5 | 12.2 |
| 3 | 85 | 117 | 0.5 | 11.3 |
| 4 | 95 | 118 | 0.5 | 18.7 |
| 5 | 94 | 118 | 0.5 | 19.6 |
| 6 | 94 | 119 | 0.5 | 21.8 |
| 7 | 94 | 120 | 0.5 | 23.8 |
| 8 | 94 | 120 | 0.5 | 21.4 |
| 9 | 91 | 121 | 0.5 | 23.5 |
| 10 | 89 | 121 | 0.5 | 21.9 |
| 11 | 93 | 122 | 0.5 | 22.7 |
| 12 | 94 | 122 | 0.5 | 20.9 |
| 13 | 93 | 124 | 0.5 | 19.1 |
| 14 | 89 | 125 | 0.5 | 20.7 |
| 15 | 89 | 127 | 0.5 | 19.6 |
| 16 | 89 | 129 | 0.5 | 19.8 |
| 17 | 89 | 134 | 0.5 | 19.4 |
| 18 | 89 | 149 | 0.5 | 20.7 |
| 19 | 89 | 165 | 0.5 | 10.4 |
| 20 | 89 | 192 | 0.5 | 14.2 |

FIG. 19 is the GLC profile for the foregoing reaction product prior to distillation.

FIG. 20 is the NMR spectrum for the major peak of the GLC profile of FIG. 19, having the structure:

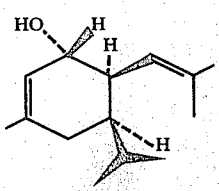

FIG. 21 is the infra-red spectrum for the major peak of the GLC profile of FIG. 19, for the compound having the structure:

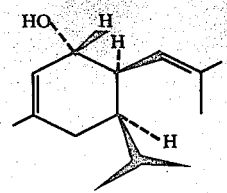

Fractions 1-20 are bulked for further reaction in Example IV and for perfume use in the following examples. Bulked fractions 1-20 have a woody, fruity, ionone-like, smokey, rosey, vetiver-like, camphoraceous, fruity and musky aroma profile.

EXAMPLE III

PREPARATION OF REDUCTION OF SUBSTITUTED METHYL ISOPROPYL CYCLOHEXENONE MIXTURE WITH HYDROGEN AND A PALLADIUM ON CARBON CATALYST

Reaction:

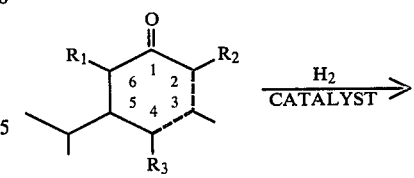

Into a 1 liter autoclave is placed 100 grams of bulked distillation of fractions 11-19 of Example I defined according to the structure:

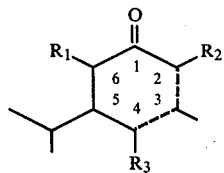

wherein the dashed lines and $R_1$, $R_2$ and $R_3$ are defined, supra. 400 ml. of anhydride isopropyl alcohol and 5 grams of 10% palladium on carbon are charged into the autoclave which is a Parr pressure shaker autoclave. The apparatus is purged several times with hydrogen. Reduction is carried out over a period of 1.5 hours at 100 psig hydrogen pressure. It is ascertained that the mole ratio of hydrogen to cyclohexenone reactant mixture is 1:1.

Infra-red, NMR, and mass spectrum analysis confirm that the reaction product is a mixture of compounds defined according to the structure:

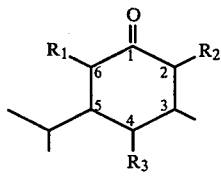

wherein $R_1$, $R_2$ and $R_3$ are defined, supra.

The reaction mass is distilled on a 12" goodloe column yielding the following fractions:

| Fraction Number | Vapor Temp. | Liquid Temp. | Vacuum mm/Hg. | Weight of Fractions |
|---|---|---|---|---|
| 1 | 70/75 | 115/115 | 0.4/0.4 | 13.3 |
| 2 | 78 | 115 | 0.4 | 14.4 |
| 3 | 71 | 112 | 0.3 | 15.6 |
| 4 | 72 | 114 | 0.3 | 20.5 |
| 5 | 73 | 115 | 0.3 | 20.0 |
| 6 | 74 | 115 | 0.3 | 19.7 |
| 7 | 74 | 116 | 0.3 | 20.2 |
| 8 | 77 | 119 | 0.3 | 27.0 |
| 9 | 80 | 121 | 0.3 | 27.1 |
| 10 | 80 | 121 | 0.3 | 25.3 |
| 11 | 80 | 121 | 0.3 | 24.8 |
| 12 | 80 | 121 | 0.3 | 22.5 |
| 13 | 80 | 122 | 0.3 | 19.2 |
| 14 | 80 | 125 | 0.3 | 16.8 |
| 15 | 82 | 130 | 0.3 | 26.5 |
| 16 | 86 | 130 | 0.3 | 26.1 |
| 17 | 91 | 131 | 0.3 | 26.1 |
| 18 | 91 | 132 | 0.3 | 23.1 |
| 19 | 93 | 171 | 0.3 | 27.2 |
| 20 | 90 | 220 | 0.3 | 10.4 |

Fractions 1-20 are bulked for subsequent use in perfumery in the perfumery and perfumed article examples, infra.

Fraction 1-20 have a herbaceous, woody, earthy, camphoraceous, tobacco resin-like, quiacwood-like, cardamom, jute-like, spicy, honey and sweaty aroma profile.

FIG. 22 is the GLC profile of the reaction product prior to distillation.

FIG. 23 is the NMR spectrum for the major peak of the GLC profile of FIG. 22 for the compound having the structure:

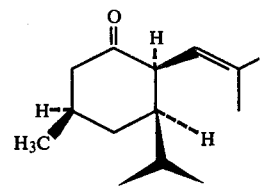

FIG. 24 is the infra-red spectrum for the major peak of the GLC profile of FIG. 22 for the compound having the structure:

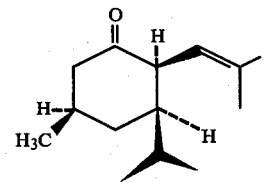

EXAMPLE IV

PREPARATION OF ACETYLATION OF CYCLOHEXENOL DERIVATIVE MIXTURE PRODUCED ACCORDING TO EXAMPLE II

Reaction:

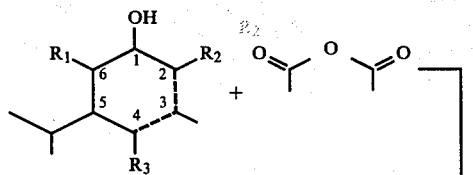

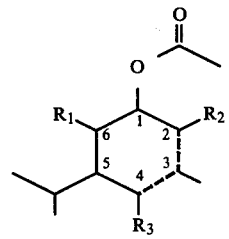

(wherein the dashed lines and $R_1$, $R_2$ and $R_3$ are defined, supra.)

Into a 2 liter reaction flask equipped with stirrer, thermometer, reflux condenser, dropping funnel and heating mantle is placed 250 ml acetic anhydride. The acetic anhydride is heated to 110° C. 324 grams of the cyclohexenol reaction product produced according to Example II defined according to the structure:

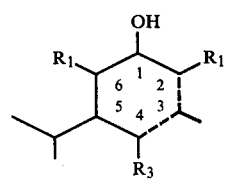

(bulked fractions 1-20) is placed in the dropping funnel. While maintaining the reaction mass at 100° C. the cyclohexenol reaction product of Example II (bulked fractions 1-20) is added to the acetic anhydride over a period of three hours. At the end of the reaction the reaction mass is stirred at 100° C. for an additional ten minutes.

The reaction mass is added to one liter of a 10% sodium chloride solution and the organic layer is then washed as follows:

(a) one 1 liter portion of 10% sodium carbonate;
(b) one 1 liter portion of water.

The reaction mass is then distilled yielding the following fractions:

| Fraction No. | Vapor Temp. | Liquid Temp. | Vacuum mm/Hg. | Reflux Ratio | Wgt. of Fractions |
|---|---|---|---|---|---|
| 1 | 49/41 | 107/105 | 3.5/3.5 | 9:1/9:1 | 6.8 |
| 2 | 46 | 105 | 0.9 | 9:1 | 14.2 |
| 3 | 46 | 105 | 0.35 | 9:1 | 12.4 |
| 4 | 47 | 112 | 0.35 | 9:1 | 13.8 |
| 5 | 77 | 115 | 0.4 | 4:1 | 18.8 |
| 6 | 88 | 127 | 0.7 | 4:1 | 20.7 |
| 7 | 94 | 127 | 0.7 | 4:1 | 20.8 |
| 8 | 81 | 128 | 0.4 | 4:1 | 19.7 |
| 9 | 87 | 129 | 0.35 | 4:1 | 20.4 |
| 10 | 86 | 130 | 0.4 | 4:1 | 20.4 |
| 11 | 86 | 131 | 0.4 | 4:1 | 20.6 |
| 12 | 86 | 131 | 0.4 | 4:1 | 18.6 |
| 13 | 86 | 133 | 0.4 | 4:1 | 18.0 |
| 14 | 86 | 135 | 0.4 | 4:1 | 17.3 |
| 15 | 86 | 140 | 0.4 | 4:1 | 15.5 |
| 16 | 88 | 160 | 0.4 | 4:1 | 14.6 |
| 17 | 90 | 193 | 0.4 | 4:1 | 12.8 |
| 18 | 84 | 245 | 0.4 | 4:1 | 9.0 |

Fractions 1-18 are bulked and utilized as such in the following perfumery and perfumed article examples.

Bulked fractions 1-18 have an ionone-like, woody aroma.

FIG. 25 is the GLC profile of the reaction product prior to distillation.

FIG. 26 is the NMR spectrum for the major peak of the GLC profile of FIG. 25 and is for the compound defined according to the structure:

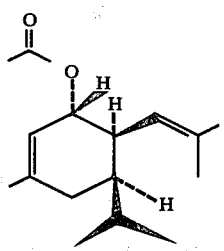

FIG. 27 is the infra-red spectrum for the major peak of the GLC profile of FIG. 25 which is for the compound having the structure:

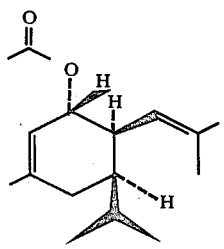

EXAMPLE V

PERFUME FORMULATION

The following sandal cologne perfume formulation is prepared:

| Ingredients | Parts by Weight |
|---|---|
| Bergamot oil | 200 |
| Orange oil | 150 |
| Lemon oil | 100 |
| Mandarin oil | 50 |
| Eugenol | 10 |
| 4-(4-methyl-4-hydroxyamyl delta³-cyclohexene carboxaldehyde | 30 |
| 3-methyl-4(2,6,6-trimethyl-2-cyclohexene-1-yl)-3-buten-2-one | 5 |
| methyl-N—3,7-dimethyl-7-hydroxy octylidene anthranilate | 5 |
| 6,7-dihydro-1,1,2,3,3-pentamethyl-4-(5H)—indanone having the structure: [structure shown] prepared according to Prep. A of Swiss Patent 523,962. | 5 |
| 2-methyl-5(2-exo-methyl-3-methylene-bicyclo-[2.2.1]-hept-2-yl)3-penten-2-ol (prepared according to U.S. Pat. No. 4,000,050 | 100 |
| Mixture of substituted cyclohexenol derivatives prepared according to Example II, bulked fractions 1-20 | 40 |

The mixture of substituted cyclohexenol derivatives prepared according to Example II in parts to the sandal cologne formulation a woody, fruity, ionone, smokey, rosey, vetiver-like camphoraceous and musky aroma nuances.

The overall aroma profile of this perfume formulation may be described as sandalwood-like with woody, fruity, ionone, smokey, rosey, vetiver and camphoraceous undertones and woody, fruity, rosey, camphoraceous and musky topnotes.

EXAMPLE VI

PERFUME FORMULATION

The following sandal cologne perfume formulation is prepared:

| Ingredients | Parts by Weight |
|---|---|
| Bergamot oil | 200 |
| Orange oil | 150 |
| Lemon oil | 100 |
| Mandarin oil | 50 |

-continued

| Ingredients | Parts by Weight |
|---|---|
| Eugenol | 10 |
| 4-(4-methyl-4-hydroxy amyl delta³-cyclohexene carboxaldehyde | 30 |
| 3-methyl-4(2,6,6-trimethyl-2-cyclohexene-1-yl)-3-buten-2-one | 5 |
| methyl-N—3,7-dimethyl-7-hydroxy octylidene anthranilate | 5 |
| 6,7-dihydro-1,1,2,3,3-pentamethyl-4-(5H)—indanone having the structure: 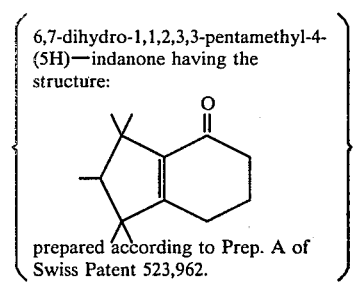 prepared according to Prep. A of Swiss Patent 523,962. | 5 |
| 2-methyl-5(2-exo-methyl-3-methylene-bicyclo-[2.2.1]-hept-2-yl)3-penten-2-ol (prepared according to U.S. Pat. No. 4,000,050 | 100 |
| Mixture of substituted cyclohexanones prepared according to Example III, bulked fractions 1-20 | 40 |

The mixture of substituted cyclohexanones (bulked fractions 1-20) produced according to Example III adds to this sandal cologne formulation an excellent herbaceous, woody, earthy, camphoraceous, tobacco resin-like, quiacwood, cardamon, jute-like, sweaty, honey and spicy aroma profile.

In combination, the overall fragrance can be described as sandalwood with herbaceous woody, earthy, camphoraceous, tobacco resin-like, quiacwood-like, cardamom and jute-like undertones and sweaty, honey and spicy topnotes.

EXAMPLE VII

LILAC PERFUME

The following mixture is prepared:

| Ingredients | Parts by Weight |
|---|---|
| Terpineol | 448 |
| Hydroxy citronellal | 133 |
| Heliotropin | 160 |
| Phenylethyl alcohol | 50 |
| Benzyl acetate | 82 |
| Anisaldehyde | 95 |
| Oil of cananga | 6 |
| Coumarin | 3 |
| Alpha ionona | 6 |
| Methyl jasmonate | 8 |
| 2,3-dimethyl-hydroquinone | 6 |
| p-methoxy acetophenone | 3 |

-continued

| Ingredients | Parts by Weight |
|---|---|
| Mixture of acetylated cyclohexenol derivatives prepared according to Example IV(bulkedfractions 1-18) | 35 |

The addition of the acetylated cyclohexenol derivative mixture prepared according to Example IV (bulked fractions 1-18) adds a woody, ionone-like aroma to this lilac perfume.

In general the lilac perfume can now be described as being lilac with woody, ionone-like undertones and more "natural-like".

EXAMPLE VIII

PREPARATION OF A COSMETIC POWDER COMPOSITION

A cosmetic powder is prepared by mixing in a ball mill 100 grams of talcum powder with 0.25 grams of the perfume substance set forth in Table II below. The resulting substance has an excellent aroma as set forth in Table II below:

TABLE II

| Substance | Aroma |
|---|---|
| Mixture of substituted cyclohexanol prepared according to Example II (bulked fractions 1-20) | A woody, fruity, ionone, smokey, rosey, vetiver, camphoraceous, musky aroma profile. |
| Mixture of substituted cyclohexenone derivatives prepared according to Example III (bulked fractions 1-20) | A herbaceous, woody, earthy, camphoraceous, tobacco resin-like, guiacqood-like, cardamom, jute-like, sweaty, honey and spicy aroma profile. |
| Acetylated cyclohexenol derivative mixture prepared in accordance with Example IV (bulked fractions 1-18) | A woody, ionone-like aroma. |
| Perfume composition of Example V | A sandalwood aroma with woody, fruity, ionone, smokey, rosey, vetiver and camphoraceous undertones and woody, fruity, rosey, camphoraceous and musky topnotes. |
| Perfume composition of Example VI | A sandalwood aroma with herbaceous, woody, earthy, camphoraceous, tobacco resin-like, guiacwood, cardamom and jute-like undertones and sweaty, honey and spicy topnotes. |
| Perfume composition of Example VII | A lilac aroma with ionone-like and woody undertones. |

EXAMPLE IX

PERFUMED LIQUID DETERGENT

Concentrated liquid detergents (lysine salt of n-dodecyl-benzene sulfonic acid as more specifically described in U.S. Pat. No. 3,948,818 issued on Apr. 6, 1976, the specification for which is incorporated by reference herein) with aroma nuances as set forth in Table II of Example VIII, supra are prepared containing 0.10%, 0.15% and 0.20% of the perfume substances as set forth in Table II of Example VIII. They are prepared by adding and homogeneously admixing the appropriate quantity of fragrance formulation as set forth in Table II of Example VIII in the liquid detergents. The detergents all possess excellent aromas as set forth in Table II of Example VIII, the intensities increasing with greater concentrations of perfume substance of Table II of Example VIII.

EXAMPLE X

PREPARATION OF COLOGNES AND HANDKERCHIEF PERFUMES

Perfumery substances as set forth in Table II of Example VIII are incorporated into colognes in concentrations of 2.0%, 2.5%, 3.0%, 3.5%, 4.0%, 4.5% and 5.0% in 75%, 80%, 85%, 90% and 95% aqueous food grade ethanol; and into handkerchief perfumes at concentrations of 15%, 20%, 25% and 30% (in 80%, 85% and 95% aqueous food grade ethanol). Distinctive and definitive aromas as set forth in Table II of Example VIII are imparted to the cologne and to the handkerchief perfume at all the levels indicated above.

EXAMPLE XI

PREPARATION OF SOAP COMPOSITIONS 100 grams of soap chips (IVORY ® produced by the Procter & Gamble Company, Cincinnati, Ohio) are mixed with one gram of each of the substances as set forth in Table II of Example VIII, supra, until homogeneous compositions are obtained. In each of the cases, the homogeneous compositions are heated under 8 atmospheres pressure at 180° C. for a period of 8 hours. The resulting liquids are placed into soap molds. The resulting soap cakes, on cooling, manifest aromas as set forth in Table II of Example VIII.

EXAMPLE XII

PREPARATION OF SOLID DETERGENT COMPOSITIONS

Detergents are prepared from the following ingredients according to Example I of Canadian Pat. No. 1,007,948, the specification for which is incorporated by reference herein:

| Ingredients | Parts by Weight |
|---|---|
| Neodal ® 45-11 (a $C_{14-15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of this detergent per sample is admixed with 0.15 grams of each of the perfume substances of Table II of Example VIII. Each of the detergent samples has excellent aromas as set forth in Table II of Example VIII.

EXAMPLE XIII

Utilizing the procedure of Example I at column 15 of U.S. Pat. No. 3,632,396 (the specification for which is incorporated by reference herein), a non-woven cloth substrate useful as a drier-added fabric softening article of manufacture is prepared wherein the substrate, the substrate coating and the outer coating and the perfuming material are as follows:

1. a water dissolvable paper as the substrate ("Dissolvo Paper);
2. Adogen 448 (melting point 140° F.) as the substrate coating; and
3. an outer coating having the following formulation (melting point about 150° F.):
   57% $C_{20-22}$ HAPS
   22% isopropyl alcohol
   20% antistatic agent
   1% of one of the perfumery substances as set forth in Table II of Example VIII.

A fabric softening composition prepared as set forth above having aroma characteristics as set forth in Table II of Example VIII consists of a substrate having a weight of about 3 grams per 100 square inches, a substrate coating weighing about 1.85 grams per 100 square inches of substrate and an outer coating weighing about 1.4 grams per 100 square inches of substrate is created, thereby providing a total aromatized substrate and outer coating weight ratio of about 1:1 by weight of the substrate. The aromas as set forth in Table II of Example VIII is imparted in pleasant manners to head spaces in the dryers on operation thereof using the drier-added fabric softening non-woven fabric articles.

What is claimed is:
1. The compound having the structure:

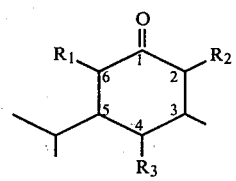

wherein one of $R_1$, $R_2$ or $R_3$ is 2-methyl-1-propenyl or 2-methyl-1-propylidenyl, and the other of $R_1$, $R_2$ or $R_3$ is hydrogen.

* * * * *